(12) United States Patent
Carter, Jr. et al.

(10) Patent No.: US 7,610,153 B2
(45) Date of Patent: Oct. 27, 2009

(54) MULTI-DRUG TITRATION AND EVALUATION

(75) Inventors: W. Hans Carter, Jr., Chesterfield, VA (US); Chris Gennings, Richmond, VA (US); Vernon M. Chinchilli, Elizabethtown, PA (US); Margaret Shih, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 520 days.

(21) Appl. No.: 10/467,835

(22) PCT Filed: Feb. 13, 2002

(86) PCT No.: PCT/US02/04086

§ 371 (c)(1),
(2), (4) Date: Feb. 2, 2004

(87) PCT Pub. No.: WO02/065120

PCT Pub. Date: Aug. 22, 2002

(65) Prior Publication Data

US 2004/0132633 A1   Jul. 8, 2004

(51) Int. Cl.
*G01N 33/48* (2006.01)
(52) U.S. Cl. .................................................... 702/19
(58) Field of Classification Search .................... 702/19
See application file for complete search history.

(56) References Cited

U.S. PATENT DOCUMENTS 4,935,450 A   6/1990   Cone, Jr.
5,647,663 A   7/1997   Holmes
5,913,310 A   6/1999   Brown
5,960,403 A   9/1999   Brown
6,186,145 B1  2/2001   Brown
6,222,093 B1  4/2001   Marton et al.

OTHER PUBLICATIONS

Berenbaum, M.C. "Direct Search Methods in the Optimisation of Cancer Chemotherapy Regimes," British Journal of Cancer (1990) vol. 61, pp. 101-109.*
Dimeo et al. "Aerobic Exercise in the Rehabilitation of Cancer Patients After High Dose Chemotherapy and Autologous Peripheral Stem Cell Transplantation," Cancer (1997) vol. 79, No. 9, pp. 1717-1722.*
Portenoy et al. "Management of Cancer Pain," The Lancet (1999) vol. 353, pp. 1695-1700.*

* cited by examiner

*Primary Examiner*—Jerry Lin
(74) *Attorney, Agent, or Firm*—Whitman, Curtis, Christofferson & Cook, P.C.

(57) ABSTRACT

Titration of a combination of drugs or treatment modalities within individual subjects is carried out using an evolutionary operation (EVOP) direct-search procedure such as the Nelder-Mead simplex. Desirability functions are incorporated to define the main response of interest and additional responses or constraints. Statistical methodology for determining whether the titrated treatment combination has resulted in an improvement in patient response and for evaluating whether a therapeutic synergism exists is also incorporated. Inferences can be made about the efficacy of the combination or about the individual drugs or treatment modalities that comprise the combination. This approach allows every patient the potential to benefit from the combination under study and permits the consideration of multiple endpoints simultaneously.

22 Claims, 12 Drawing Sheets

MULTI-DRUG TITRATION AND EVALUATION

BACKGROUND OF THE INVENTION

1. Field of the Invention

The invention generally relates to the titration of multi-modality therapy regimens. In particular, the invention provides methods of titrating and evaluating multi-modalitiy therapy regimens using an evolutionary operation (EVOP) approach.

2. Background of the Invention

The use of multiple medications and/or treatment modalities in the treatment of individual patients is an increasingly commonplace occurrence. The elderly population, who consume the most drugs and in whom relative drug consumption continues to increase, is rapidly growing in the United States and other developed nations. The pace of new drug development, from drug discovery to drug production, has accelerated greatly, and single diseases are now treated with multiple drugs targeting different biochemical pathways or different aspects in the pathophysiology of a disease. This increase in drug consumption brings with it a dramatic increase in the potential for drug interactions and adverse drug reactions. New approaches to treatment and prescribing are needed to address these increasingly complicated dosing regimens.

Dose titration with single compounds is a relatively straightforward process employed by physicians to identify appropriate dose levels which produce improved responses in patients while simultaneously minimizing the adverse side effects a patient may experience. After taking into account a patient's age, weight, and other factors specific to the patient, the physician will prescribe an initial dose which may be increased or decreased as needed, depending on how the patient responds. This titration continues until a favorable balance between the desired response and undesirable side effects is achieved.

The difficulty arrives in attempting to translate this approach to determining dosages in the case where multiple drugs and/or other treatment modalities are being prescribed in the treatment of a single disease, or where the consideration of multiple endpoints is needed in the case where a single treatment is prescribed. There is currently no systematic or efficient method for determining dosages in multi-drug regimens. The physician generally either chooses to address the problem empirically, or will employ an ad-hoc approach, varying the levels of one drug while keeping the doses of all the other drugs in the combination fixed. Unfortunately, this approach does not account for potential interactions among the drugs, which may be crucial when searching for the most desirable therapy.

Not only is combination dosing difficult for practicing physicians in the day-to-day care of their patients, but it also presents a problem in both clinical trials research and drug evaluation research. For example, in the evaluation of a novel two-drug combination, which is composed of a new therapy plus the standard therapy, a typical approach which may be used is to randomize half of the subjects to the standard drug group and the other half to the two-drug combination. There are several problems with this approach. The first problem is that if no difference in response is found between the groups, this does not necessarily mean that the new combination is ineffective. The lack of effect may lie in the dose chosen for use in the study. Secondly, this approach does not provide any information regarding the location of more effective doses if the combination is not found to differ from the standard. On the other hand, if the new combination is found to be more effective, approximately half the subjects enrolled in the study, those randomized to the standard treatment, have not benefitted from the trial. Finally, even with early stopping rules, the time a patient spends on the inferior treatment can have lasting detrimental effects. These problems can lead to difficulties with patient recruitment and adherence to the study protocol.

Outside of the clinical trials arena, a common approach which has been used to evaluate combination therapies is the use of response surface methodology (RSM). With this approach, an experiment is carried out using a grid of fixed dose combinations. The fixed combinations are administered to subjects, often using a factorial design, and the response is observed over the range of dose combinations. The resulting response surface can then be used to identify areas of improved response. While this is a somewhat effective approach, it is limited in its application for several reasons. Firstly, this approach requires the use of predetermined, fixed combinations, none of which may actually correspond to the best treatment. Also, the ideal treatment may lie entirely outside of the range of doses used in the study. Furthermore, these studies quickly become expensive due to the numerous dose combinations required. Finally, RSM requires the pre-specification of the dose-response relationship, which is usually unknown. This requires an additional assumption that the dose-response relationship is well approximated by the equation specified.

It would be highly desirable to have available a systematic and efficient, yet practical and flexible, method for titrating in individual patients treatment regimens comprised of multiple modalities, and for evaluating the efficacy of such multi-modality therapies.

SUMMARY OF THE INVENTION

The present invention provides methodology for titrating a multi-modality therapy regimen in a subject or in a plurality of subjects. In order to carry out the invention, an appropriate combination of p modalities (for example drugs, radiation, quantifiable amounts of psychotherapy or physical therapy, or other treatment modalities) is selected by a skilled practitioner (e.g. a physician). In a preferred embodiment of the invention, $p \geq 2$. However, the methodology of the present invention may also be applied to the titration of a single modality. The combination may be selected to treat a specific disease condition, or may be directed to the treatment of a group of symptoms typically associated with more than one disease condition.

Drawing upon extant clinical knowledge, a skilled practitioner then develops p+1 dose combinations for the selected modalities, i.e. the practitioner proposes p+1 different combinations of reasonable beginning dosage levels for each modality in the combination. It is further necessary to identify at least one potential clinical endpoint to monitor. The endpoint is one that might reasonably be predicted to occur as a result of the administration of the modality, and the endpoint must be ordinal in nature, i.e. it must be possible to rank order the outcomes from worst to best. The endpoint may also be quantifiable in nature (for example, amenable to a direct numeric measurement) but this is not a necessary condition for the practice of the present invention.

The method also involves the formation of a geometric representation (i.e. a geometric figure) of the dose combinations used in the titration. In one embodiment of the present invention, the geometric figure is a simplex which may be represented by a geometric figure with p+1 vertices. Each of the p+1 vertices of the simplex corresponds to one of said p+1 dose combinations.

A composite desirability function for each of said p+1 dose combinations may be determined in the following manner: a particular dose combination is administered to the subject during a predetermined period of time and a measurement of each endpoint is obtained at the end of the indicated time period. The measurements obtained for a given response are assigned to a desirability function. The desirability function may be continuous and differentiable, and must map the measurements to a [0,1] interval where 0 represents a least desirable response and 1 represents a most desirable response. The individual desirability functions are then combined into a composite desirability function and each resulting composite desirability function is associated with the vertex of the simplex corresponding to that particular drug combination. An evolutionary operational direct search algorithm is applied to the simplex. The EVOP procedure is applied to determine the location in dose space that represents a suggested next dose combination by identifying the vertex corresponding to the least desirable composite desirability function and moving from that vertex through dose space to a new location. The new location is the vertex of a new simplex and should be associated with a more desirable outcome. If the new vertex is not associated with a more desirable outcome, future simplexes will move away from this point and as a result the titration process is in that sense self-correcting. The other vertices retain their original locations. The new dose combination is then administered to the subject, the subject's responses are determined and assigned to desirability functions as described, and a new composite desirability function is computed for the new combination. The EVOP procedure is again applied as described above and a next suggested dose combination is determined. This procedure is performed repeatedly until a predetermined criteria is fulfilled. For example, the procedure may be carried out: until a given number of new dose combinations have been generated, administered and the results analyzed; or for a given length of time; or until a predetermined composite desirability function value is attained.

It is also possible in the practice of the present invention, to monitor a single endpoint rather than multiple endpoints. In this case, it is not always necessary to assign the measurements of a response to a desirability function. Rather, the measurements obtained at each dose combination may be associated with a vertex of the geometric figure and the EVOP procedure may be applied as described above. An example would be if the end point was simply a decrease in blood pressure. However, if a target desirability function has been established for the therapy regimen, it is possible to utilize such a desirability function for only a single endpoint. An example would be if the endpoint was to attain a blood pressure of a specific value, or within a specific range.

In a preferred embodiment of the present invention, the evolutionary operational direct search algorithm that is applied is the Nelder-Mead algorithm. However, other direct search algorithms may also be utilized, for example, direct search algorithms based on the construction of complexes rather than simplexes. (See, for example, Box, 1965 and Box, 1969). The advantage of utilizing direct search algorithms is that the use of derivatives is not required, so that no assumptions need be made regarding the underlying relationships between the modalities which are administered and the endpoints being observed.

The titration methods of the present invention may be utilized for combined modality therapies that may be active in treating any of a number of diseases and/or conditions, examples of which include but are not limited to cancer, AIDS, arthritis, diabetes, hypertension, and the like. Further, there are diseases and conditions which are currently treated with a single modality which may in the future be treated with more than one modality. All such conditions are intended to be encompassed in the practice of the present invention.

In one embodiment of the present invention, the desirability function which is utilized is continuous and differentiable. However, as a result of the use of direct search algorithms, this need not be the case. However, the desirability function must map the measurements obtained to a [0,1] interval. In a preferred embodiment of the invention, the desirability function is obtained from the logistic cumulative distribution function such as that described by Gibb (1998). The composite desirability function may involve the use of weights for the individual desirability functions.

The invention further provides a computerized system including a computer program for carrying out the methods of the present invention. The system includes means for entering into a computer a number p of modalities to be used in the regimen, means for generating a simplex as described, means for determining the composite desirability functions, and means for outputting a new, next dose combination.

DETAILED DESCRIPTION OF THE PREFERRED EMBODIMENTS OF THE INVENTION

Figure 1A:
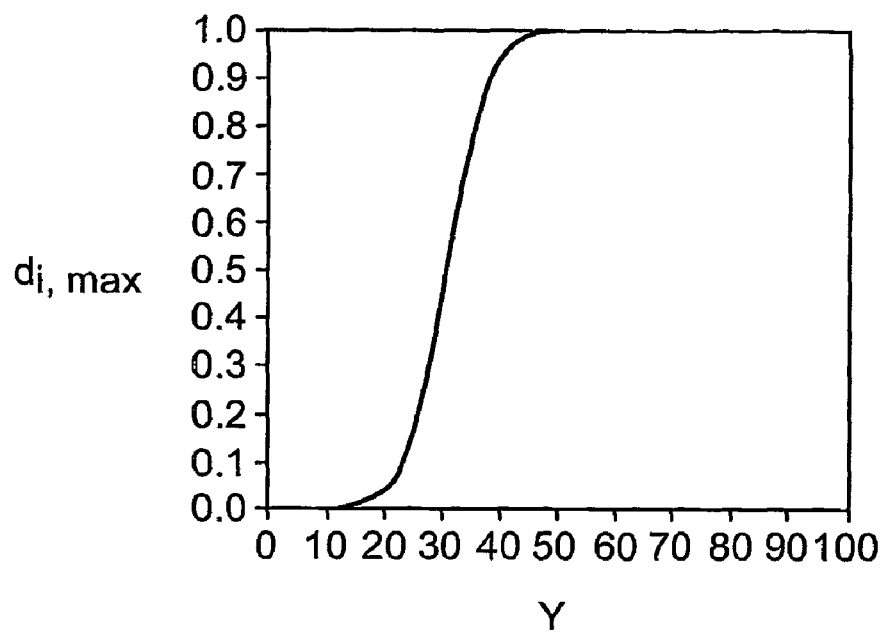
FIG. 1A-C. Example of a maximizing desirability function (A), a minimizing desirability function (B) and a target desirability function (C). This latter function if the product of the maximizing desirability function, $d_{i(max)}$ shown in 2A, and the minimizing desirability function, $d_{i(min)}$ shown in 2B.

The present invention provides systematic and efficient methodology for titrating combination drug and/or other treatment modality therapies within individual patients and for evaluating the efficacy of such multi-modality therapies. The methods are practical and flexible, and take into account potential interactions between modalities. The methodology uses an evolutionary operation (EVOP) direct-search procedure to titrate doses within individual patients. The EVOP approach is used to climb through the dose space to a location of improved patient response. Statistical methodology is also utilized for determining whether there has been an improvement in response to a treatment regimen, and whether a therapeutic synergism exists among the modalities comprising a multi-modality regimen.

In one embodiment of the present invention, the treatment modalities which are titrated are drugs. However, those of skill in the art will recognize that many other treatment modalities exist which are suitable for inclusion in the practice of the present invention. Such modalities include but are not limited to radiation therapy; quantifiable amounts of modalities such as physical therapy, psychotherapy, exercise regimens, acupuncture, skeletal or other body manipulations (e.g. chiropractic manipulation, massage therapy, the wearing of braces, the immobilization of limbs, and the like); nutritional therapy (e.g. administration of vitamins or nutriceuticals); gene therapy techniques, and the like. To that end, a "dose" is herein defined as the quantity of a modality that is administered, and may be a dose in the classical sense (e.g. a dose of a substance such as a medication measured as a number of pills, or a quantity of liquid, etc.). Alternatively, a dose may be a defined as an amount of a modality that is quantified in terms of time (e.g. hours of psychotherapy per week, minutes exercising at a particular heart rate, or meditating, and the like), or repetitions of a treatment modality (e.g. one session of massage therapy, chiropractic manipulation, or acupuncture, and the like).

In some embodiments of the present invention, the purpose of the titrations methods described herein may be to determine the optimal treatment regimen for a patient in order to alleviate the symptoms of a disease. However, those of skill in the art will recognize that other applications may also exist which do not involve the treatment of a disease per se. For example, a patient may exhibit symptoms of more than one disease, or of symptoms which are not readily assignable to a particular disease, or of side effects that result from the modalities being administered. Further, some undesirable conditions may not necessarily be categorized as "disease" but would still be amenable to analysis using the methods of the present invention, e.g. a multi-modality treatment regimen for weight loss, or to optimize multi-modality interactions in healthy subjects in clinical trials. In addition, the methods may also be utilized for purposes such as to determine a maximum tolerated dose, for example, in a cancer treatment regimen. The methods may also be utilized in both human and non-human patients.

EVOP Direct Search Methods

In a preferred embodiment of the present invention, an evolutionary operational (EVOP) method is utilized to carry out the titration. Traditional applications of EVOP have involved the use of factorial designs (Fisher, 1935; Yates, 1935; D. R. Cox, 1958; and Snedecor and Cochran, 1980) to introduce variations in the operating conditions. EVOP makes improvements to the resulting product and has proven useful in optimizing multidimensional relationships without requiring specification of either a model or distribution (Box, 1957; Box and Draper, 1969; Spendley, Hext, and Himsworth, 1962). Whereas response surface methods are a static research technique, evolutionary operation can be applied as a continuous and automatic production-line method. Hunter and Kittrell (1966) present an extensive review of various industrial applications of EVOP, most of which take place in the chemical industry, although applications in the automotive and food industries are also discussed. For a more detailed, in-depth discussion of EVOP techniques, one is referred to the text by Box and Draper (1969).

As an example of how EVOP would work in practice, suppose one is optimizing the response of an ongoing industrial manufacturing process, and that the response to be optimized is the yield of chemical product. The yield of the product would be continuously monitored, as would the operating conditions, which might consist of the temperature, pressure, and amount of starting material. Minor variants in the operating conditions are then introduced in a factorial pattern. When a significant change in the yield is found in either a positive or negative direction, the operating conditions which produced the change in yield can be identified and subsequently adjusted in the direction of optimizing the yield. The monitoring process would then resume and could be continued indefinitely.

Two of the most appealing aspects of EVOP are the simplicity with which it can be carried out and the fact that it is conducted as an inherent part of a normal process, not as an artificially conducted experiment. The everyday application of EVOP techniques does not require the input of professional mathematicians or statisticians, and after the initial setup, the EVOP process can continue indefinitely, with new variables being added or old variables being removed at any time.

There are several issues which arise in adapting EVOP, in its original form, to the problem of finding therapeutic treatment combinations which result in an improved outcome status in individual patients. The first problem is that traditionally, EVOP requires the use of many design points. Use of a factorial design would require the introduction of multiple small variations in treatment dosages which would be applied continuously to each patient. This presents obvious ethical problems regarding patient treatment, which overshadow other relatively minor issues of patient compliance and inefficiency in the design.

A second problem arises from the traditional application of a statistical test of significance to determine whether movement should be made to a new experimental region. Movement to a new dose region would not be made until there was statistical evidence that this would result in an improved patient response. In this case, the patient would be given multiple but varying doses of the drug combination within a limited dose range. The same set of doses would be repeatedly administered until there was evidence that changing the dose levels would benefit the patient. While it is appropriate that changes to the dose levels should not be made until there is some apparent benefit to be gained, this is again inefficient and results in a slower optimization process.

An automatic EVOP procedure, which is more easily adapted to the clinical arena, was introduced by Spendley, Hext, and Himsworth (1962). Their sequential simplex method, a modification of Box's original approach, is automatic, does not utilize a factorial design, and does not require hypothesis testing before each movement. Instead, they use a direct search method approach to optimizing multiple factors. Direct search methods are a group of procedures also referred to as hill-climbing or steepest ascent procedures, which are often used for minimizing or maximizing functions. A direct search method allows one to search for improved conditions while a process is occurring by observing the effects of small, deliberate changes in the operating conditions which result in a type of forced or artificial evolutionary process. Pre-specification of the dose-response relationship is not necessary, one is not limited to predetermined combinations, and compounds can be added or removed from the combination under study at any time.

This initial simplex EVOP method was later modified by Nelder and Mead (1965), who developed a more flexible method termed the Nelder-Mead Simplex procedure. Their method has the advantage of allowing the simplex to accelerate and adapt to the contour to the response surface. Segreti (1977) has discussed the use of the Spendley, Hext, and Himsworth EVOP method in combination chemotherapy studies, and more recently, Berenbaum (1990) has discussed another modified approach, the partition method, in relation to the problem of optimizing cancer chemotherapy regimens in animal studies. Box also modified the procedure, creating complexes and incorporating constraints (1965). However, all of these applications refer to patients or animals randomized to a single treatment group and do not discuss dose optimization within individual patients.

In the practice of the present invention, EVOP has been effectively adapted to the clinical setting where a combination of modalities is being used for treatment or being evaluated for efficacy. While the multidimensional dose-response relationship is unknown, it can be observed at specific treatment combinations, and a predetermined algorithm can be followed to adjust the therapeutic doses toward improving patient outcome. For example, a patient may make periodic visits to a physician who monitors the patient for improvements in outcome in response to the multiple modalities being prescribed. The physician or researcher can use an EVOP direct search procedure to adjust the doses comprising the treatment combination in response to the patient's continuously evolving condition. The titration is carried out within each patient, allowing every patient to benefit from the therapy if there is any benefit obtainable.

The practice of the present invention involves carrying out a within-patient titration. In a preferred embodiment, the within-patient titration uses the Nelder-Mead algorithm, which is more flexible than the Spendley, Hext, and Himsworth method, permitting acceleration and adaptation to the response surface. However, those of skill in the art will recognize that other flexible direct search EVOP algorithms may also be utilized in the practice of the present invention.

In one embodiment of the invention, in order to extend the flexibility of this approach, a continuous desirability function may be utilized (Gibb, 1998), which incorporates both the main response of interest and additional responses or constraints, as the overall measure of response. In this way, the main response or responses may be improved while simultaneously satisfying multiple additional constraints.

Description of Desirability Functions

The desirability function approach was developed by Harrington (1965) and later modified by Derringer and Suich (1980). Gibb (1998) extended the methodology to desirability functions which are continuous and differentiable. Desirability functions have been successfully used in the industrial setting. Each response of interest is assigned to a continuous desirability function (which may be continuous and differentiable), di, with values ranging from 0 to 1, where a value of 0 designates the response as not at all desirable, while a value of 1 is assigned to the most desirable response. The index i represents the ith desirability function or the ith response of interest. The basic shape of the function is determined by whether one is trying to maximize or minimize the response, or aim for a range of target values. The exact shape of each desirability function is determined in collaboration with physicians or other experts knowledgeable about the disease under study and the therapeutic effects of the treatments being administered.

In one embodiment of the present invention, a logistic cumulative distribution function (Gibb, 1998) was used for the desirability, but any function which maps the response to the [0,1] interval could be used. With the logistic function, the form of the 'bigger-is-better' or maximizing desirability function (Gibb, 1998) is $$d_{i(max)} = \left[1 + \exp-\left(\frac{Y_i - a_i}{b_i}\right)\right]^{-1}$$

where $$a_i = \frac{(Y_i^* + Y_{i*})}{2}, \quad b_i = \frac{Y_i^* + Y_{i*}}{2\ln\left(\frac{1-\gamma_i}{\gamma_i}\right)}, \quad Y_{i*} < Y_i^*, \text{ and } \gamma_i \in (0, 1).$$

The parameter $a_i$ is an average of the upper ($Y^*_i$) and lower ($Y_{i*}$) bounds of the response level being targeted, $b_i$ controls the function spread, and γi is such that $d_i(Y_{i*})=\gamma i$ and $d_i(Y^*_i)=1-\gamma i$. The 'smaller-is-better' or minimizing desirability is obtained simply by reversing the sign of the exponential argument, having the resulting form, $$d_{i(min)} = \left[1 + \exp-\left(\frac{Y_i - a_i}{b_i}\right)\right]^-$$

Figure 1B:
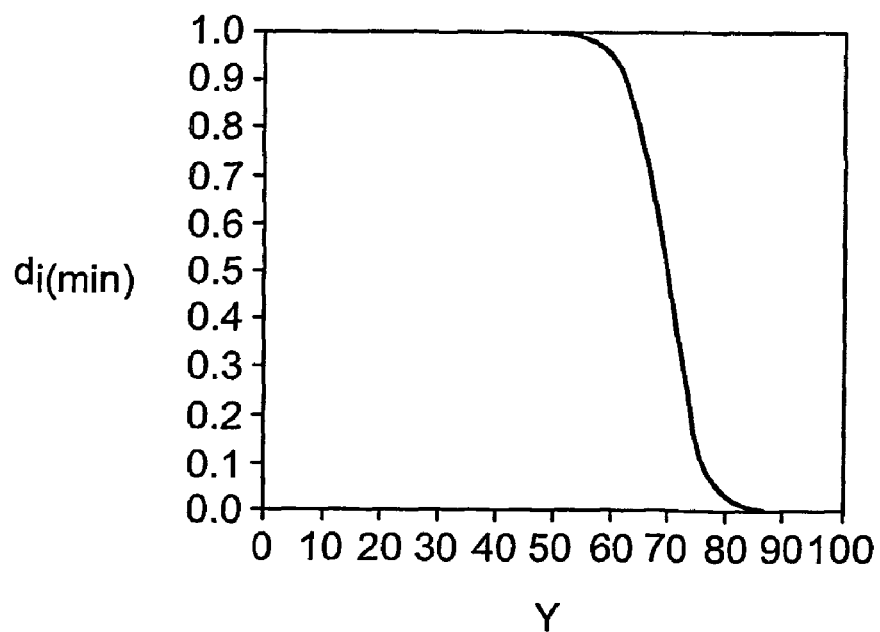

Examples of a maximizing and a minimizing desirability faction are given in FIGS. 1A and 1B, respectively.

Figure 1C:
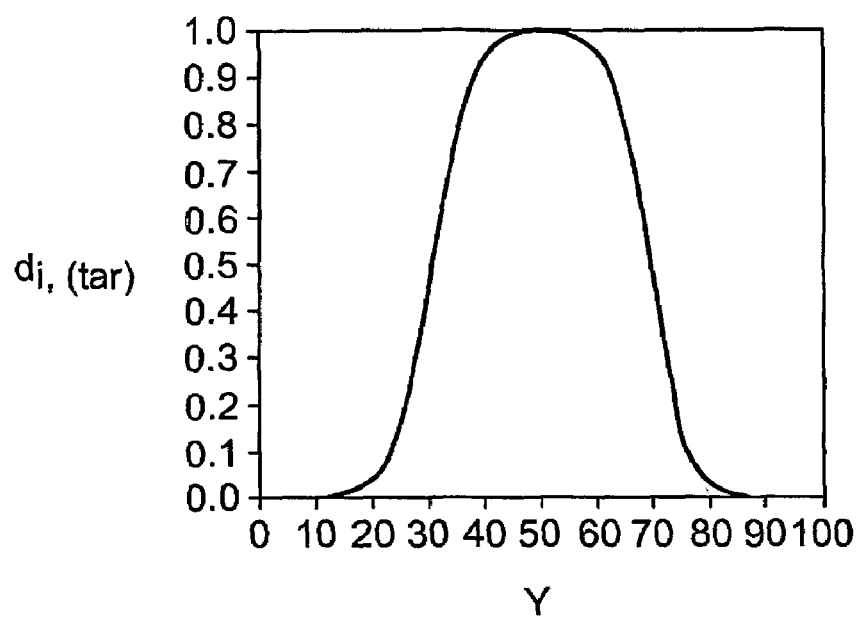

A 'target' desirability function, such as shown in FIG. 1C, can then be constructed by multiplying a set of desirability functions, such as a minimizing desirability and a maximizing desirability to give $d_{i(target)}=d_{i(max)} \times d_{i(min)}$. This allows the researcher to incorporate asymmetry into the desirability function. The parameters $a_i$, $b_i$, and $\gamma_i$ allow the researcher flexibility in defining the desirability function and the degree of conservativeness to incorporate. These individual desirability functions can then be combined using the geometric mean to arrive at a single continuous measure of the overall composite desirability, D, such that $D=(d1*d2* \ldots *dk)^{1/k}$. Derringer (1994) has also described the use of weights, in the specification of the desirability function, so that different responses can be assigned different levels of importance.

Each response is weighted by an exponent, wi, so that the composite desirability with weights has the form $$D=(d_1^{w1} d_2^{w2} \ldots d_k^{wk})^{1/\Sigma wi}, i=1, \ldots, k.$$

In a preferred embodiment of the present invention, unweighted desirability functions are utilized. However, those of skill in the art will recognize that weighted desirability functions may also be employed. This may occur, for example, if a skilled practitioner determines that a particular endpoint is of more import than others. The desirability function representing this endpoint can then be suitably weighted.

Figure 2A:
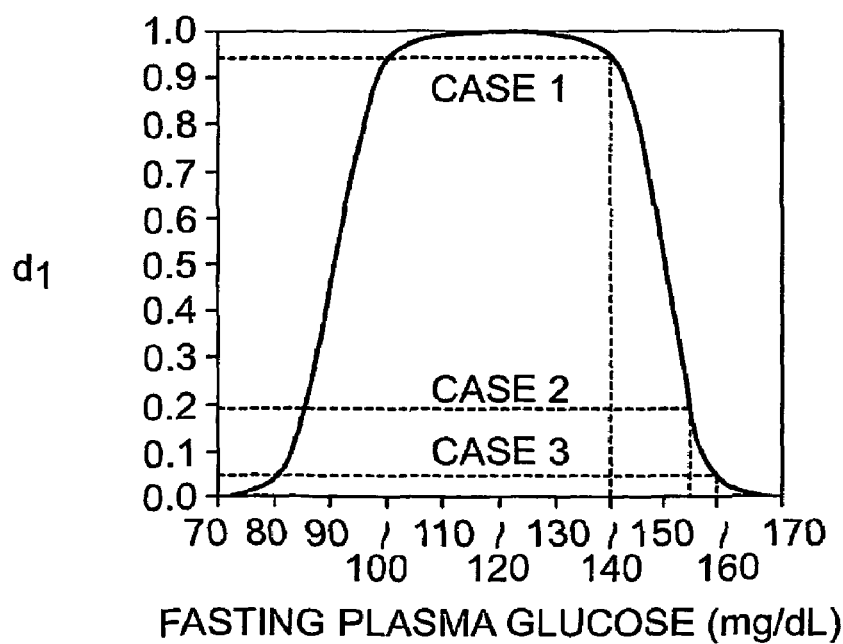
FIGS. 2A and B. Examples of desirability functions; A, target desirability function for fasting plasma glucose where $(Y_{1*}', Y_1^*)=(80,100)$, $(Y_{1*}'', Y_1^{*''})=(140, 160)$, $\gamma_1=0.05$, $d_1=d_1'*d_1''$; B, minimizing desirability function for increase in body weight, where $Y_{2*}=20$, $Y_2^*=40$, $\gamma_2=0.05$.
Figure 2B:
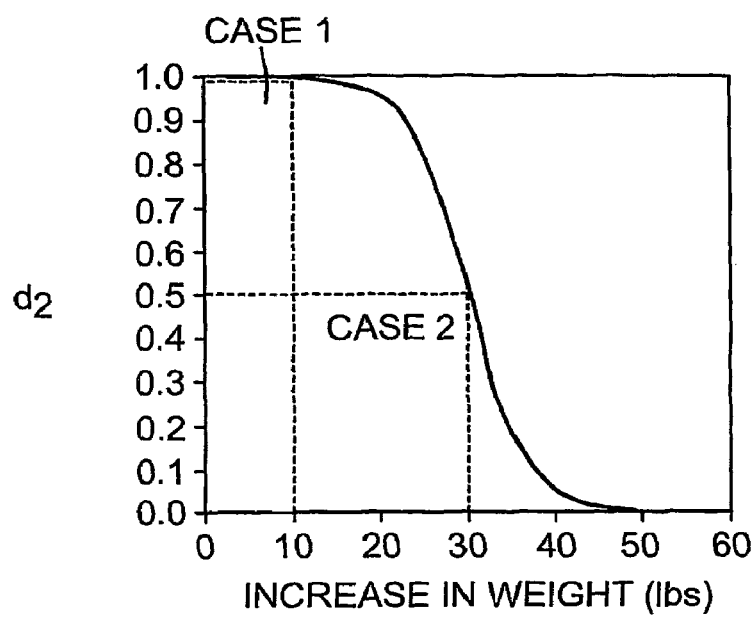

As an example, consider the case where a physician is treating a type 2 diabetes patient with a combination of a sulfonylurea and metformin. There are numerous clinical endpoints the physician may monitor, including fasting plasma glucose (FPG), glycosylated hemoglobin levels (HbA1c), the patient's lipid profile, weight, and blood pressure, and the number of adverse gastrointestinal and hypoglycemic events the patient experiences. For any or all of these endpoints, a specific target, maximizing, or minimizing desirability function can be assigned and incorporated into the composite desirability function. Note that this method tends to weight small desirability values heavily so that if any of the individual desirabilities are small, the overall desirability remains small. As a simple case, suppose we only wish to monitor two endpoints, the patient's fasting plasma glucose (FPG) and the patient's body weight. Suppose we would like to target the patient's FPG to be within the 80-140 mg/dL range. Additionally, we want to minimize the increase in weight the patient may experience due to the treatment. Example desirability functions for each response are specified in FIGS. 2A and 2B.

Table 1 describes three cases which could occur. In Case 1, the patient has reasonable fasting plasma glucose values and has experienced minimal weight gain. Referring to the desirability functions specified in FIGS. 2A and 2B, the glucose value of 140 corresponds to a desirability (d1) of 0.95, and the weight gain of 10 corresponds to a desirability (d2) of 1. This gives an overall desirability (D) of 0.98. This high desirability suggests that the patient is doing well with the current treatment. In the second case, the patient has a less desirable glucose value of 155, which corresponds to a desirability of 0.19, and a weight gain of 30 lbs, which corresponds to a desirability of 0.5. This patient has an overall desirability of 0.31, which indicates that changes to the patient's current therapeutic regimen may be needed to improve the treatment of this patient. The last example is of a patient with a high serum glucose value which is further outside the desirable limits, corresponding to a desirability of 0.05, but one who has experienced no weight gain and so has a weight gain desirability of 1. Although this patient is doing well in terms of preventing weight gain, the glucose level is objectionably high, so the overall desirability decreases to 0.22.

TABLE 1

Desirability example for differing fasting plasma glucose and weight gain levels. $D = (d_1 * d_2)^{1/2}$

|  | FPG (mg/dL) | $d_1$ | Weight Gain (lbs) | $d_2$ | D |
|---|---|---|---|---|---|
| Case 1 | 140 | 0.95 | 10 | 1.0 | 0.98 |
| Case 2 | 155 | 0.19 | 30 | 0.5 | 0.31 |
| Case 3 | 160 | 0.05 | 0 | 10. | 0.22 |

The application of desirability functions to within-patient titration can be useful for both the multiple drug case and the single agent case where multiple endpoints are being monitored. In the single agent case, desirability functions can provide the physician or researcher with a more objective way of evaluating the overall effect of a therapy and can provide information about individual clinical endpoints and side effects. In the multiple drug case, by combining desirability functions with EVOP direct-search methods, we can titrate combination therapies within individual subjects and make inferences about the efficacy of the combination.

Titration Procedure

Once the individual desirability functions are defined, they are incorporated into the overall composite desirability function, which becomes the response undergoing optimization during the titration process. In our simulations, the Nelder-Mead simplex algorithm was used to carry out the within-patient titration. The first step of the procedure is to establish an initial simplex, a geometric figure with a fixed number of vertices. In the p-dimensional case, where p is the number of drugs comprising the combination under evaluation, the number of vertices required for the simplex is p+1. At each step, the simplex adapts its form, moving away from the vertex with the lowest response toward the direction of maximum response.

Figure 3:
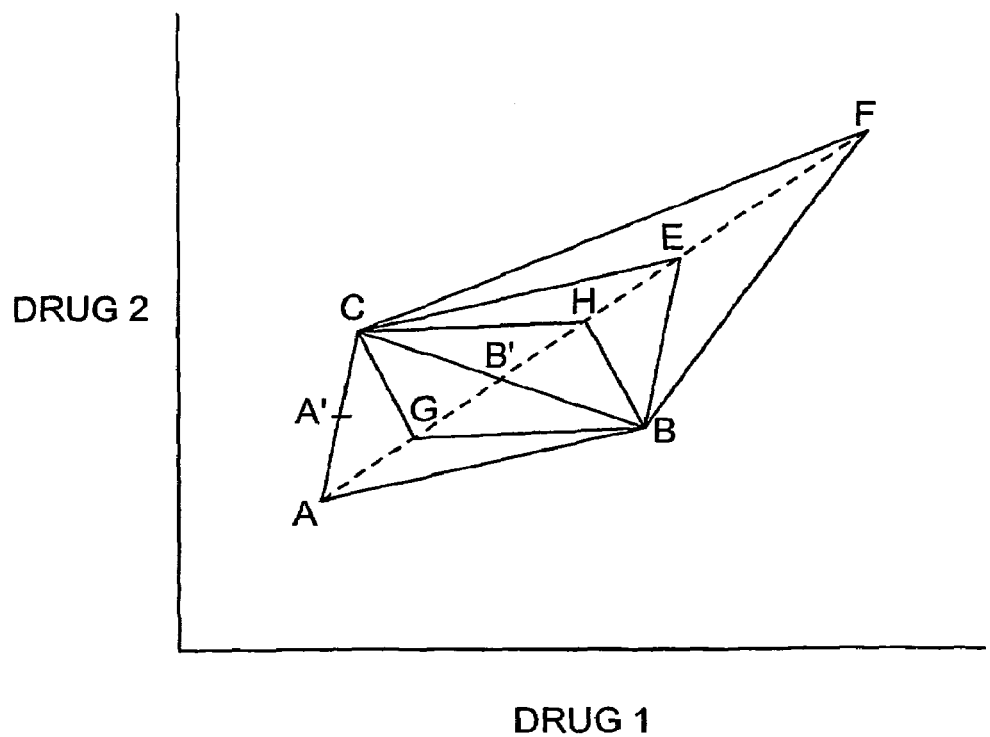
FIG. 3. Nelder-Mead simplex ABC with possible subsequent points.
Figure 4A:
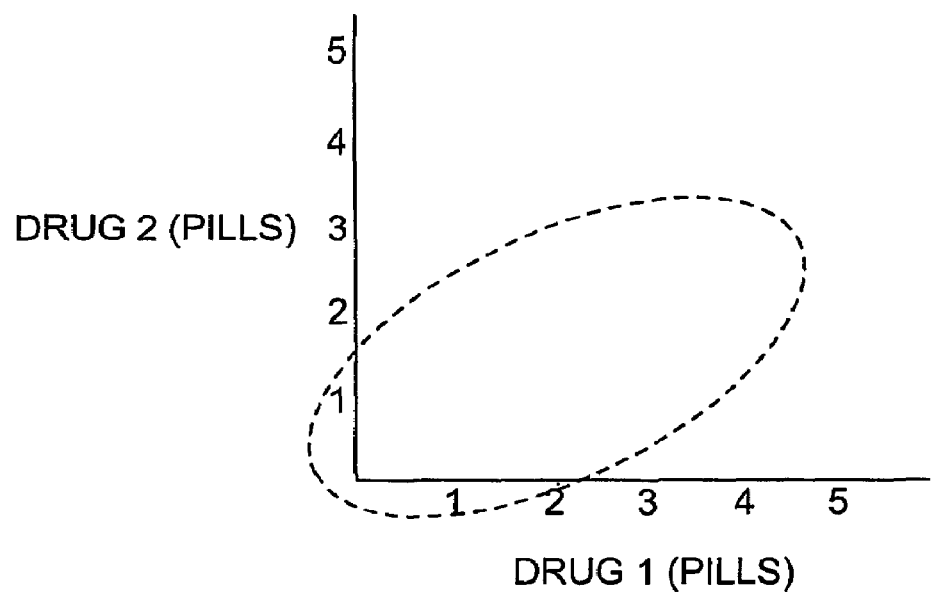
FIG. 4A-D. Evaluating confidence ellipsoids: A, confidence ellipsoid contains the origin; B, confidence ellipsoid contains both axes but not the origin; C, confidence ellipsoid contains only one axis; D, , confidence ellipsoid does not contain either axis or the origin.
Figure 4B:
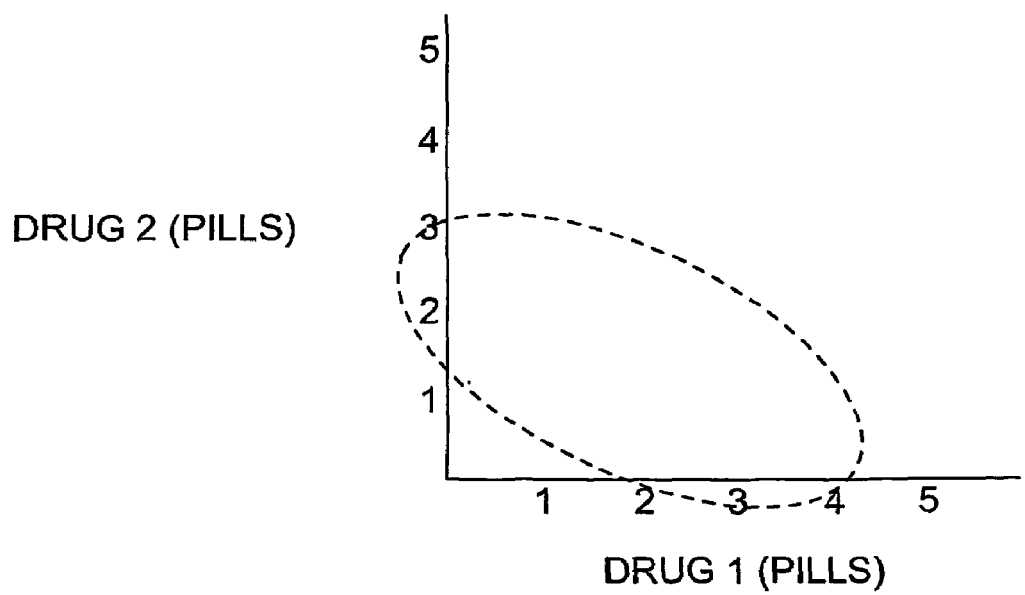
Figure 4C:
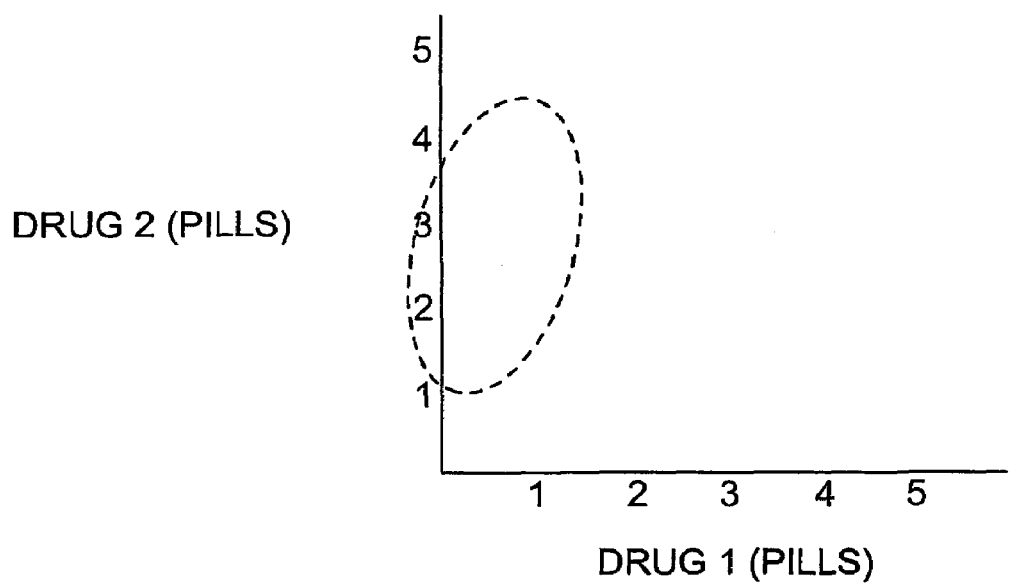
Figure 4D:
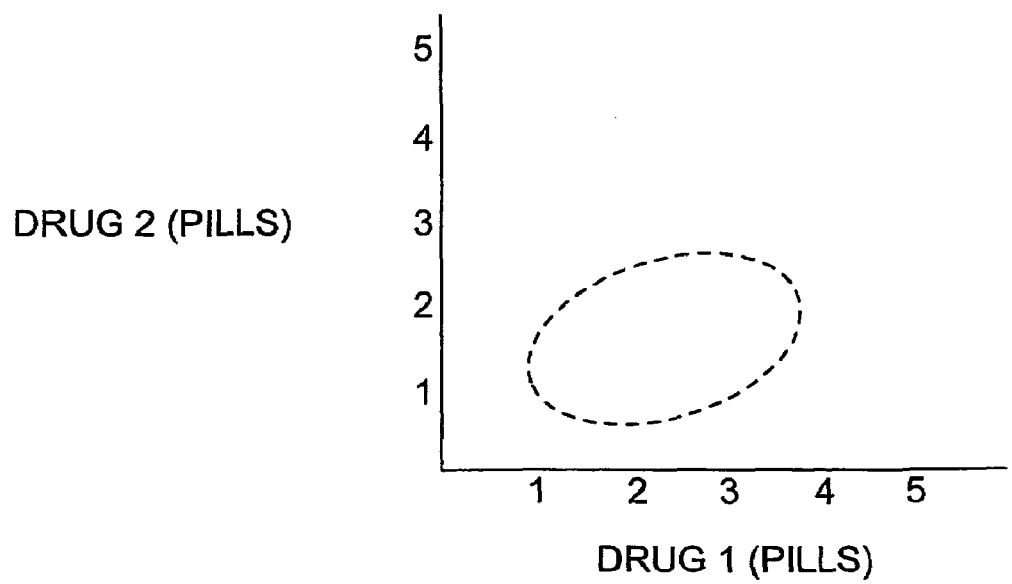

This is most easily illustrated in the two-dimensional case where the simplex is a triangle. Each vertex A, B, and C of the triangle (FIG. 3) represents a different dose level of the two-drug combination. At the initial step, the subject's response is measured at each of these three dose combinations, and the composite desirability resulting from the administration of each combination is compared, with the simplex reflecting away from the least desirable response, through the centroid of the face created by the remaining vertices to a new point. In addition to reflection, the simplex can also extend, contract, or perform a shrinkage contraction, depending on the contour of the response surface (see Table 2).

TABLE 2

Conditions governing the formation of subsequent simplex. (Adapted from Olsson and Nelson, 1975).

| Condition | Action | New Simplex |
|---|---|---|
| $f(C) \leq f(E) \leq f(B)$ | Reflect | BCE |
| $f(E) \leq f(C)$ | extend | BCF |
| $f(A) \leq f(E)$ | Contract | BCG |
| $f(B) \leq f(E) \leq f(A)$ | Contract | BCH |
| $f(A) \leq f(G)$ or $f(E) \leq f(H)$ | Shrink | A'B'C |

The Nelder-Mead algorithm is run on a continuous scale, and therefore the new dose combination determined by the algorithm is not given in units of whole pills or whole dose units. To enhance the practicability of the EVOP titration approach, the dose combinations are adjusted to whole units (e.g. whole pills). The new dose combination to be administered is determined by either rounding to the nearest whole dose unit, or more conservatively, by rounding down to the dose unit.

The initial simplex step size, which specifies how far apart the initial dose combinations are, and the reflection and expansion coefficients used by the Nelder-Mead procedure, which determine how far the simplex can move or expand in one step, are decided in collaboration with the physician expert, and can be modified to be more or less conservative depending on factors such as the therapeutic index of the drug involved. The step size of the initial simplex will depend on the potency and toxicity of the drugs under study, with smaller initial step sizes prudent for compounds of higher potency and/or toxicity. In the case where the drugs are already being used in combination in practice, a reasonable starting combination would be the number of pills or dose units with which the practicing physician generally initiates therapy. With a new and yet untested combination of drugs, where one cannot draw from previous experience, a more conservative approach is advisable.

Each subject begins the process by being evaluated at each of the p+1 combinations of p drugs in the regimen. The subject receives the initial combination and the response is recorded. The subject then receives the second combination, which is determined by the initial step size, and the response is measured after a time interval sufficient to preclude carryover effects. This continues for each of the p+1 drug combinations. It should be noted that in the situation where there is a lengthy time to response, EVOP may not be practical due to the time required in setting up the initial simplex. After the initial simplex is established, the new simplex is formed, determining the next dose combination to be administered. This process repeats until the subject has passed through a fixed number of steps or until other specific stopping criteria are reached and further titration is deemed unnecessary. The simplex movement can be continuously monitored by the physician, and the reflection, expansion, and contraction coefficients can be modified if the simplex expands to a dose with which physician is uncomfortable. Otherwise, a dose constraint can be put in as a boundary to prevent the simplex from moving above a certain dose in one or more dimensions. At the final step, the last simplex is evaluated and the combination producing the most desirable response is determined to be the 'best' treatment combination. Possible stopping criteria include running the process until convergence to a 'best' treatment or until an 'acceptable' response is reached. Since disease processes are dynamic and often chronic, the physician may continue to periodically monitor subjects after the initial optimized dose level is reached, and may restart the titration process if changes in the patient's status are observed.

Inference about the Patient Population

The methodology of the present invention may also be applied to the analysis of multi-modality therapies in a large test population. In this case, it is desirable to test for both an improvement in response after all subjects have passed through the titration process and to test the efficacy of the combination or individual components of the combination. After a group of subjects has passed through the titration process, the initial and final dose locations and corresponding initial and final responses are used to determine whether there has been an improvement in response and whether a therapeutic synergism exists among the drugs comprising the combination. The set of final treatment dose combinations observed from the n subjects enrolled in a study can be considered a sample from a multivariate distribution.

The first goal can be accomplished by identifying it as a one-sample location problem on paired responses which can easily be addressed using existing tests, which are described below. The second goal can be accomplished by construction of a p-dimensional confidence ellipsoid about the central location of the 'cloud' of final dose combinations in the p-dimensional dose space. Both a parametric approach and non-parametric approach are described below. Based on the estimated confidence ellipsoid, we can evaluate whether a therapeutic synergism (Mantel, 1974) exists between all treatments comprising the combination, and we can also estimate a region of improved therapy (Carter, 1982).

The One-Sample Location Problem

To test for an improvement in response, it is possible to apply the Wilcoxon Signed Rank Test (Wilcoxon, 1945) or Fisher Sign Test (Fisher, 1925). The following are defined: $diff_i = y(k)_i - y(0)_i$, $i=1, \ldots, n$, where $y(k)_i$ is the response of the ith subject after undergoing k steps of the titration process and $y(0)_i$ is the response of the ith subject at baseline. For the signed rank statistic, we assume the $diff_i$ are independent and each comes from a common distribution symmetric about $\delta$. The following hypothesis is tested:

$$Ho: (\delta \leq 0) \text{ vs. } H1: (\delta > 0),$$

where without loss of generality, an increase in response indicates improvement. Forming the absolute differences $|diff_1|, \ldots |diff_n|$ and letting $R_i$ denote the rank of the absolute differences in the joint ranking from least to greatest of $|diff_1|, \ldots, |diff_n|$, we define $$\psi_i = 1 \text{ if } (diff_i > 0), \psi_i = 0 \text{ if } (diff_i < 0), \text{ and } i=1, \ldots, n$$

and $$B = \sum_{i=1}^{n} \psi_i$$

A large sample approximation is:

$$T^* = \frac{T^* - \left[n\frac{(n+1)}{4}\right]}{\sqrt{\left[n(n+1)\frac{(2n+1)}{24}\right]}} \sim N(0, 1).$$

Thus, we reject $H_o$ if $T^* \geq Z_\alpha$.

For the Sign Test, we assume the $diff_i$ are independent and each comes from a distribution with median $\delta$. We wish to test the hypothesis: $H_o: (\delta \leq 0)$ vs. $H_1: (\delta > 0)$ We define $$T^+ = \sum_{i=1}^{n} R_i \psi_i$$

where $\psi_i$ is defined as above, so that B is the number of positive $diff_i$'s. We reject Ho if $B \geq Bin(\alpha, n, \frac{1}{2})$, where Bin $(\alpha, n, \frac{1}{2})$ satisfies $$Po[B \geq Bin(\alpha, n, \frac{1}{2})] = \alpha.$$

Rejection of the hypothesis of 'no improvement' indicates that the titration process has been successful in finding a dose combination which improves the patient's response from a baseline response. The responses used in these tests are from the desirability functions discussed above. Therefore an improved response indicates not only an improvement in the primary endpoint of interest but improvement in the overall health status of the patient, as defined by the physician through the desirability function. Determination of sample size and power requirements for the Wilcoxon signed-rank and Fisher sign tests are detailed in Lehmann (1975).

Construction of the Confidence Ellipsoid About a Multivariate Location

A region of improved therapy may be estimated based on the estimated confidence ellipsoid about the location of the multivariate distribution of each individual's final treatment combination. If the combination treatment includes p elements, the multivariate sampling model involves n independent, identically distributed p-component random vectors $x_1, \ldots, x_n$, each with the p-variate distribution function, where $F(t_1-\theta_1, \ldots, t_p-\theta_p)$, where F is absolutely continuous with continuous marginal distribution functions $F_1(t_1-\theta_1), \ldots, F_p(t_p-\theta_p)$. The vector of location parameters $\theta=[\theta_1, \theta_2 \ldots \theta_p]$ contains the marginal medians, and if each Fj is symmetric, $\theta$ is also the vector of marginal means.

A parametric inferential approach would be to assume a form for F and to construct the confidence ellipsoid for $\theta$. One obvious choice of distribution is the multivariate normal. Let $x_1, x_2, \ldots, x_n$ be a p-variate sample which is i.i.d. $N_p(\theta=[\theta_1, \theta_2 \ldots \theta_p]', \Sigma)$. The maximum likelihood estimate for $\theta$ is $$\bar{x} = \frac{1}{n}\sum_{i=1}^{n} x_i$$

and an unbiased estimate Morrison, 1976) for $\Sigma$ is $$S = \frac{1}{n-1}A$$

where $$A = \sum_{i=1}^{n}(x_i - \bar{x})(x_i - \bar{x})'.$$

Since $\sqrt{n}(\bar{x}-\theta) \sim N_p(0, \Sigma)$, replacing $\Sigma$ with its consistent and unbiased estimate and recalling the relationship between Hotelling's T2 and the F distribution, an exact $100(1-\alpha)\%$ confidence ellipsoid for $\theta$ is $$\left\{\theta : n(\bar{x} - \theta)' S^{-1}(\bar{x} - \theta) \leq \frac{(n-1)p}{n-p} F_{1-\alpha;p,n-p}\right\}.$$

For small or medium-sized samples, a more robust approach, which does not require distributional assumptions, would be to construct a confidence ellipsoid about the multivariate median. An efficient estimator of $\theta$ associated with Wilcoxon's Signed Rank statistic is the Hodges-Lehmann estimator based on ranks (Hodges and Lehmann, 1963). Let $x_1, x_2, \ldots, x_n$ be a p-variate sample which is i.i.d. F such that the p-vector of marginal medians for F is $\theta=[\theta_1, \theta_2 \ldots \theta_p]'$ and F is diagonally symmetric about $\theta$. We can estimate $\theta$ using signed rank statistics (Hettmansperger, 1984). Let $\hat{\theta}_j$ be the p-vector of the sample medians of Walsh averages (Tukey, 1949) with components $$\hat{\theta}_j = \text{median}\left\{\frac{(x_{ij}+x_{i'j})}{2}, 1 \leq i \leq i' \leq n\right\}, j=1, \ldots p.$$

if $W_{(1)j} \leq W_{(2)j} \leq \ldots \leq W_{(N)j}$, are the ordered Walsh averages, where $N=n(n+1)/2$, the $100(1-\alpha)\%$ confidence interval for $\theta_j$ is $[W_{(a_j+1)j}, W_{(N-a_j)j}]$, where $a_j$ can be approximated by $$a_j \approx \frac{n(n+1)}{4} - 0.5 - z_{1-\frac{\alpha}{2}}\sqrt{\frac{n(n+1)(2n+1)}{24}}$$

Finding $\hat{\theta}_j$, is equivalent to finding $\theta_j$ such that the signed rank statistic $$T_j(\theta_j) = \sum_{i=1}^{n} \frac{R_{ij}\theta_j}{n+1}\text{sign}(x_{ij} - \theta_j)$$

is approximately equal to zero, where $R_{ij}\theta_j$ is the rank of $|X_{ij}-\theta_j|$ among $|X_{1j}-\theta_j|, |X_{2j}-\theta_j|, \ldots, |X_{nj}-\theta_j|$. Then $$\sqrt{n}(\hat{\theta}_w-\theta) \rightarrow^D N_p(0, \Gamma_w^{-1}v_w\Gamma_w^{-1})$$

where $\Gamma_w = \text{Diag}(\gamma_{w,1}, \ldots, \gamma_{w,p})$ such that $$\gamma_{w,j}=2\int_{-\infty}^{\infty}f_j^2(x)dx, j=1, \ldots, p,$$

and $v_w$ is a pxp matrix such that $$v_{w,jj'}=4\int_{-\infty}^{\infty}\int_{-\infty}^{\infty}F_j(x_j)F_{j'}(x_{j'})dF_{jj'}(x_{j-xj'})-1, 1 \leq j \neq j' \leq p$$

and $v_{wjj}=\frac{1}{3}$ (Hettmansperger, 1998). A consistent estimate of $\gamma_{wj}$, $j=1, \ldots p$ is found from the asymptotic length of a confidence interval for $\theta_j$ based on the Walsh averages (Lehmann, 1975)

$$\hat{\gamma}_{w,j} = \left(\frac{\left(4z_{1-\frac{\alpha}{2}}\right)}{\sqrt{12n}\left(W_{(N-a_j)j}, W_{(a_j+1)j}\right)}\right)$$

When the variability is such that a large proportion of subjects arrives at the same, or similar, final dose locations, an inordinate number of ties results due to the effect of rounding to whole units. As a consequence, $W_{(a_j+1)j}$ and $W_{(N-a_j)j}$ become identical, and the confidence interval for $\theta_j$, $[W_{(a_j+1)j}, W_{(N-a_j)j}]$, goes to zero. To correct for this, we use the smallest viable interval of $2\epsilon=0.5$ as the lower limit for $W_{(a_j+1)j}-W_{(N-a_j)j}$ such that $$\hat{\gamma}_{w,j} = \left(\frac{\left(4z_{1-\frac{\alpha}{2}}\right)}{\sqrt{12n}\,(0.5)}\right)$$

A consistent estimate of $v_{wjj'}$, $j, j'=1, \ldots, p$ (Hettmansperger, 1998), is $$\hat{v}_{w,jj'} = \frac{1}{n}\sum_{i=1}^{n}\left\{\frac{R_{ij},(\hat{\theta}_{w,j})}{n+1}\right\}\left\{\frac{R_{ij},(\hat{\theta}_{w,j'})}{n+1}\right\}\text{sign}(x_{ij}-\hat{\theta}_{w,j})\text{sign}(x_{ij'}-\hat{\theta}_{w,j'})$$

Replacing $v_w$ and $\Gamma_w$ with consistent estimates, an approximate $100(1-\alpha)\%$ confidence ellipsoid for $\theta$ is $$\{\theta : n(\hat{\theta}_w-\theta)'[\hat{\Gamma}_w^{-1}\hat{v}_w\hat{\Gamma}_w^{-1}]^{-1}(\hat{\theta}_w-\theta) \leq \chi_{1-\alpha,p}^2\}.$$

After the confidence ellipsoid is established, the ellipsoids can be evaluated using the approach described by Carter, et al. (1982). The confidence ellipsoid is evaluated along a grid of points on each single axis. As an illustration, in the 2-dimensional case, it is determined whether the ellipsoid a) contains the origin, implying the combination is not different from no treatment at all; b) contains both axes but not the origin, implying that treatment with the combination is better than having no treatment, but that the same response could be obtained by using either drug by itself; c) contains only one axis, implying that treatment with the combination is no better than treatment with the single drug, or d) does not contain either axis, implying the presence of a therapeutic synergism, that the combination of drugs produces a greater response than either drug alone (FIG. 4).

In a preferred embodiment of the instant invention, the evolutionary operation direct search titration methodology is suitably applied to the treatment of chronic conditions or diseases with long time courses. This allows sufficient time for the establishment of the initial simplex and for titration to a maintenance therapy. Since disease processes are dynamic, EVOP can be continued indefinitely to track the patient's progress. After an initial maintenance dose is identified, the physician can continue to periodically monitor the patient, and the titration process can be restarted when changes to the patient's status are observed. Those of skill in the art will recognize that the characteristics of a condition which would favor the use of the methods of the present invention include but are not limited to those having an easily and rapidly measured response, a lengthy time; and a condition where dose escalation within a patient is reasonable. Examples of diseases or syndromes which may benefit from this treatment approach include but are not limited to hypertension, diabetes, rheumatoid arthritis, asthma, AIDS, and some cancers.

In a preferred embodiment of the present invention, the responses being monitored are easily measurable and reproducible. For example, they might consist of laboratory tests or measurements that are already performed periodically as part of the regular standard of care so as to minimize additional discomfort or inconvenience to the patient. Accuracy and reproducibility of measurement are also important to ensure that the simplex is moving purposefully according to the clinical endpoint (or signal) rather than moving haphazardly in response to a large variability in the measurement (or noise). Some examples of suitable clinical endpoints include but are not limited to blood pressure, fasting plasma glucose, forced expiratory volume, the reported number of side effects a patient is experiencing each week, and the like. Those of skill in the art will recognize that many suitable endpoints exist which may be measured in the practice of the present invention, and all such endpoints are intended to be encompassed in the scope of the instant invention.

In the situation where a lengthy time to response is required, the use of EVOP may not be appropriate. A sufficient time interval between measurements must be allowed to preclude any carryover effects from the previous treatment. Otherwise, the time required to set up the initial simplex may become impractical, and the subsequent simplex movement may be too slow to be of benefit in treating the patient. EVOP titration may also be problematic when the number of therapies in a combination is extremely large. In this case, establishing the initial simplex may become cumbersome due to time constraints, and problems with patient compliance are more likely. EVOP may also be of limited application when the course of a disease is too brief to provide substantial information. Theoretically, there is no limit to the number of different modalities which can be titrated by the methods of the present invention. Limitations on the number will likely arise rather as a result of practical clinical considerations and will be determined by a skilled practitioner on a case by case basis.

In a preferred embodiment of the instant invention, multi-modality therapies are titrated by the methods of the present invention. However, those of skill in the art will recognize that the techniques are also applicable to the titration of a single drug.

The present invention also contemplates a computer program for use in carrying out the practice of the present invention. Such a computer program could be written and adapted for use in any of many known devices which are employed by suitable practitioners of the invention, for example, physicians. Examples of such devices include but are not limited to PCs, laptop computers, palm pilots, pocket PCs, personal digital devices, and the like. Further, many such devices are also currently under development.

Details of exemplary embodiments of the methodology are given in the examples below, but should not in any way be considered limiting.

EXAMPLES

Example 1

A Comparison of Multi-drug Titration with Glyburide and Metformin to Treatment with Glucovance It is estimated that approximately 16 million people in the U.S. have diabetes, only one third of which are diagnosed. Type 2 diabetes accounts for 90-95% of all patients diagnosed with diabetes. An additional 15 million people have impaired glucose tolerance, putting them at a high risk for developing type 2 diabetes. Diabetes is currently the 4th leading cause of death by disease in the U.S., the leading cause of blindness in adults 20-74 years old, and the leading cause of end-stage renal disease. Sixty to seventy percent of diabetics have some form of mild to severe neuropathy, and diabetes is associated with a 2 to 4 fold increase in risk for both heart disease and stroke. The considerable morbidity and mortality associated with this disease is estimated to cost $98 billion each year in direct medical costs and indirect costs to industry (Centers for Disease Control, 1998).

Recent reports (UKPDS Group, 1998; Diabetes Control and Complications Trial Research Group, 1993) have added to the evidence that tighter glycemic control may delay or prevent both macrovascular disease and microvascular and neuropathic complications. Therefore it is of significant interest, both from the point of view of reducing morbidity and mortality and of controlling health care costs, to find the most efficient strategy for applying our current arsenal of diabetes therapies to achieve the tightest glycemic control.

In recent years, several new oral therapeutic agents have been introduced to treat diabetes, which has opened up new options for managing this disease. Diabetes treatment is typically first approached by recommending changes to both diet and activity levels. If treatment with lifestyle changes alone is unsuccessful, the physician has a choice of several oral agents that may be added alone or in combination to the treatment plan, including sulfonylureas, biguanides (metformin), alpha-glucosidase inhibitors and the thiazolidinediones.

The current therapeutic approach to treating type 2 diabetes is often first to find an effective dose with a single drug and then to incrementally increase levels of the drug to maintain the effect as time progresses. Currently, all type 2 diabetes treatments show secondary failure over time (UKPDS group, 1996; Riddle, 1997) with HbA1c levels increasing by 0.2 to 0.3 percent per year (UKPDS group, 1996). Therefore, all treatments must be subject to continuous adjustment and periodic increases. When the maximum dose of the single drug is reached or the single drug is no longer sufficient to maintain acceptable glucose levels, a new compound is often added to keep serum glucose measurements within the allowable range while keeping the first compound at its maximum dose. Such an approach, however, does not account for potential interactions among the drugs, and it is possible that the patient is not receiving the best available treatment. In addition, several studies have examined the use and benefits of combination therapies, including the combination of sulfonylureas with metformin (Defronzo and Goodman, 1995; Hermann et al. 1994; Bell and Mayo, 1997), and there is some evidence that these drugs, used in combination, provide better glucose control than either drug by itself (Defronzo and Goodman, 1995; Hermann et al. 1994). One company, Bristol-Myers Squibb, has combined the sulfonylurea, glyburide, with the biguanide, metformin, into a single tablet, recently approved and currently sold in the U.S. under the name Glucovance.

The sulfonylureas are a group of agents that increase insulin secretion by stimulating pancreatic beta cells (Lebovitz, 1992). They are effective in lowering glycemia in about 50 percent of patients who are unable to control their glycemia with diet and exercise alone (Ertel, 1997). The effectiveness declines as the failure of the beta cells progresses, resulting in a secondary failure rate of 3 to 10 percent per year (Ertel, 1997). The average decrease in HbA1c is 1 to 2 percent (Pharmacological intervention in: Medical management of type 2 diabetes. 1998). There is a small risk of hypoglycemia with use of the sulfonylureas and a modest associated weight gain. The effects on the lipid profile are minimal, with minor decreases in triglyceride levels. Treatment should be initiated at the lowest recommended dose and increased every four to seven days until the desired effect or maximum dose is reached.

Glyburide is a second generation sulfonylurea, administered twice a day in doses ranging from 1.25 mg to 5 mg, with a maximum daily dose of 20 mg.

Metformin is the only biguanide currently approved for use in the U.S. by the FDA. It acts on the liver to decrease hepatic glucose production and also promotes insulin sensitivity in both the liver and peripheral tissues (UKPDS Group, 1998). Treatment with metformin has been shown to decrease fasting and postprandial glycemia by 60-70 mg/dL (Cusi and DeFranso, 1998), with an average decrease in HbA1c of 1.5 to 2 percent (Cusi and DeFranso, 1998). Metformin shows initial effectiveness in approximately 75 to 80 percent of type 2 diabetes patients (Lebovitz, 1992) and does not cause hypoglycemia. It is associated with less weight gain than the sulfonylureas (UKPDS Group, 1998) and is often used in combination with the sulfonylureas or with other agents. It also appears to have favorable effects on the lipid profile and is associated with small decreases in total cholesterol, LDL and triglyceride levels (Lebovitz, 1994). There are some gastrointestinal side effects, most notably nausea or diarrhea, which can be minimized by taking metformin with meals, and by initiating treatment at a low dosage and increasing the dose slowly over a period of several weeks. The most serious side effect is lactic acidosis (Lebovitz, 1995), particularly in patients with impaired renal function. Therefore, metformin cannot be used when the creatinine clearance is greater than 1.4 mg/dL in women, and greater than 1.5 mg/dL in men. Metformin is also contraindicated in cardiac failure and pulmonary disease patients or anybody with a disease condition which interferes with lactate removal. Treatment with metformin is usually initiated at a dose of 500 mg, which may be increased in 500 mg increments every one to two weeks, with the maximum effect seen at a dose of 2000 mg per day.

Glucovance is a combination of the sulfonylurea, glyburide, and the biguanide, metformin. It has been approved for use both as an initial adjunct therapy to diet and exercise and a second-line therapy in patients who have not successfully controlled their hyperglycemia with diet, exercise, or treatment with a sulfonylurea or metformin alone. Glucovance is available in fixed combination doses of 1.25 mg glyburide/250 mg metformin, 2.5 mg/500 mg, and 5 mg/500 mg, with a maximum daily dose of 20 mg/2000 mg. An unpublished study of 806 previously untreated type 2 diabetes patients, summarized on the package insert (Bristol-Myers Squibb, 2000), found a mean change from baseline HbA1c of 1.48% at 20 weeks of treatment with Glucovance 1.25 mg/250 mg compared to a mean change from baseline of 1.24% for glyburide, and 1.03% for metformin. Information from another unpublished study, also summarized on the Glucovance package insert, involved 639 type 2 diabetes patients whose blood sugar was inadequately controlled with sulfonylureas alone. These patients were either given glyburide 20 mg, metformin 500 mg, Glucovance 2.5/500 mg, or Glucovance 5/500 mg. At the end of 16 weeks, the mean HbA1c value of patients given either dose of Glucovance was reported as 1.7% lower than those treated with glyburide alone, and 1.9% lower than those treated with metformin alone (Bristol-Myers Squibb, 2000; Medical Letter Inc., 2000).

The current ADA Guidelines for Glycemic Control (American Diabetes Association, 1999) are:
Preprandial Glucose 80-120 mg/dL
Bedtime Glucose 100-140 mg/dL
HbA1c<7%

A logistic regression analysis was performed using data from the study of 806 drug-naive type 2 diabetes patients printed in the package insert ((Bristol-Myers Squibb, 2000) to determine whether there was an interaction effect between the 2.5 mg of glyburide and 500 mg of metformin. The likelihood ratio $\chi 2$ statistic associated with the test of additivity (i.e. no interaction) was 5.975, with a p-value of 0.0145, indicating the presence of a significant interaction between the two drugs. In addition, the coefficient of the interaction term was negative ($-0.887$), indicating that the interaction was antagonistic between the two drugs at the given doses. It should be noted that these were the starting doses given to the patients for a period of 4 weeks, after which the dose could be increased up to a maximum of four tablets daily.

This initial analysis emphasizes the need for a more systematic yet flexible approach to combination dosing. Presumably these two drugs, glyburide and metformin, are used in combination with the goal that they interact synergistically, or at least in an additive fashion. However, this analysis indicates that with the doses used in the study, the two drugs appear to be antagonistic to each other, rather than synergistic or additive.

In order to improve the analysis of the administration of glyburide and metformin, the methodology of the present invention may be applied as follows:

A 20 week pilot study is conducted. Ten newly diagnosed type 2 diabetes patients, men and women, are enrolled using the following eligibility criteria:
Inclusion Criteria
  Men and women newly diagnosed with type 2 diabetes and receiving no current or previous pharmacological treatment
  HbA1c<10%
  Informed Consent
Exclusion Criteria
  Women who are pregnant or nursing
  Subjects who have previously been treated with other diabetes therapies
  Subjects with hepatic or renal impairment (creatinine>1.4 mg/dL in women, >1.5 mg/dL in men)

Subjects with concomitant CHF or pulmonary disease

Each subject begins the study by rotating through each of three starting drug combinations. Before beginning treatment, baseline values of fasting plasma glucose (FPG), 2-hour postprandial plasma glucose (PPG), fingerstick HbA1c, and HbA1c are recorded. The patient is randomized to one of six sequences of initial dose combinations: ABC, ACB, BAC, BCA, CAB, or CBA where A=one 2.5 mg tablet glyburide, one 500 mg tablet metformin, B=two 2.5 mg tablets of glyburide, one 500 mg tablet metformin, or C=one 2.5 mg tablet glyburide, two 500 mg tablets metformin. Each dose combination is administered for a period of 2 weeks. The patient is instructed to keep a daily journal of his or her fasting glucose measurements and 2-hour postprandial glucose measurements. At the end of the first treatment period and each subsequent two week period, the fasting glucose measurements and 2-hour postprandial glucose measurements, recorded by the patient over the previous one week, are reported to and averaged by the physician, along with a fingerstick HbA1c measurement. In addition, the number of reported hypoglycemic episodes and the number of reported negative GI effects over the previous one week are also recorded. Unless an office visit is requested by the patient at the end of each treatment period, the averaged fasting and 2-hour postprandial glucose measurements, the fingerstick HbA1c, the number of hypoglycemic episodes, and the number of GI complaints are reported to the physician over the telephone at the end of the second week. The measurements are combined into a single desirability measure (Appendix 4.A) and the Nelder-Mead algorithm (Appendix 4.B) is used to determine the next dose combination to be administered to the patient. If the physician is uncomfortable with the algorithm determined dose, the physician adjusts the dose, and the actual dose prescribed by the physician is recorded, together with the algorithm determined dose. The following treatment dose is again determined by the Nelder-Mead algorithm, using the adjusted dose information.

The study continues for a period of 20 weeks. The dose combination for each patient is titrated until an average fasting glucose of <150 or an average 2-hour postprandial glucose of <180 is achieved or until the end of the study period. After a maintenance dose is established, bimonthly reports with data collection and monitoring will continue for the duration of the study period.

Laboratory Studies

BP, ALT, serum creatinine, cholesterol, HbA1c (initial and final visit), fingerstick HbA1c Data Collection and Monitoring The patient keeps a diary of daily fasting glucose and 2-hour postprandial glucose measurements. The measurements recorded by the patient over the previous one week will be averaged and recorded at each visit. Fingerstick HbA1c is also measured at each visit. Serum HbA1c is measured at the initial visit and final visit.

Example 2

Simulation Studies Examining the Effectiveness of the EVOP Multi-drug Titration Algorithm in Dosing a Combination of Therapeutic Agents Simulation studies were carried out using the estimated dose response surface from a published multicenter, factorial design clinical trial conducted by Burris, et.al. (1990), which studied the efficacy of the combination therapy of the diuretic hydrochlorothiazide (HCTZ) and a slow-release formulation of diltiazem hydrochloride (DLTZ), a calcium channel blocker, in the treatment of mild to moderate hypertension. The trial was conducted over a period of six weeks, following a 4- to 6-week placebo 'run-in' period. A 4 by 5 factorial grid of treatment doses was used, with 4 twice-a-day doses of hydrochlorothiazide ranging from 0 to 25 mg, and 5 twice-a-day doses of diltiazem hydrochloride ranging from 0 to 180 mg. Mild-to-moderate essential hypertension was defined as supine diastolic blood pressure in the range of 95 to 110 mm Hg. The goal of treatment was to achieve a supine diastolic blood pressure of less than 90 mm Hg, with no limiting adverse experience. 261 patients completed the six-week treatment protocol, with 13 to 17 patients randomized to each treatment group.

Using Proc RSREG in SAS, Version 6.12 (SAS Institute, Cary, N.C.)25, data from the plots published in the study were used to generate the response surfaces for the three main variables of interest: diastolic blood pressure (DBP), 4.16+ 1.60×HCTZ+0.39×DLTZ−0.12×2HCTZ+0.020×2DLTZ− 0.033×HCTZ*×DLTZ; serum cholesterol (CHO), 0.12+ 0.092×HCTZ+0.033×DLTZ−0.0073×2HCTZ−0.0032× 2DLTZ−0.0013×HCTZ*×DLTZ; and serum glucose (GLU), −0.12+0.076×HCTZ−0.011×DLTZ-0.00011×2HCTZ+ 0.0030×2DLTZ−0.0011×HCTZ*×DLTZ. The dose units were converted from milligrams to whole pill counts. One pill was equivalent to 3.125 mg of HCTZ or 15 mg of DLTZ.

Figure 5A:
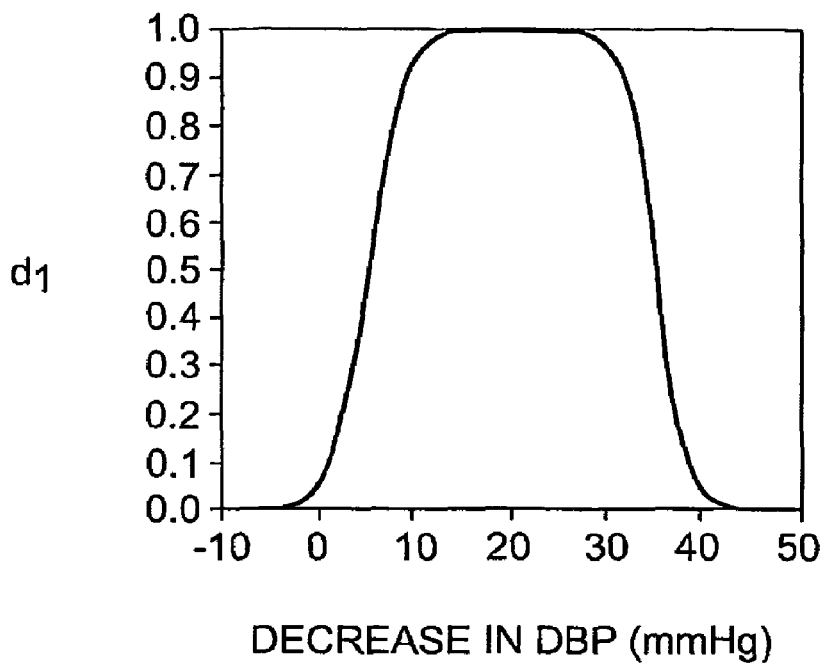
FIG. 5A-C: A, Target desirability function for diastolic blood pressure (d1). This function is a product of a minimizing desirability function (d1') with parameters $Y1^{*'}=0$, $Y1^{*'}=10$, $\gamma 1'=0.05$, and a maximizing desirability function (d1") with parameters $Y1^{*''}=30$, $Y1^{*''}=40$, $\gamma 1''=0.05$. B, Minimizing desirability function for increase in cholesterol (d2) with parameters $Y2^*=11.6$, $Y2^*=27.1$, $\gamma 2=0.05$. C, Minimizing desirability function for increase in serum glucose (d3) with parameters $Y3^*=7.2$, $Y3^*=14.4$ mmol/L, $\gamma 3=0.05$.
Figure 5B:
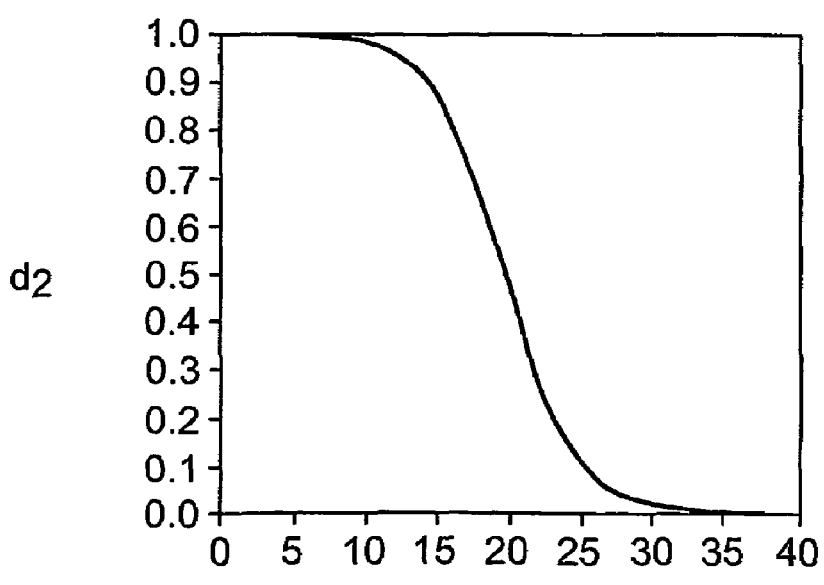
Figure 5C:
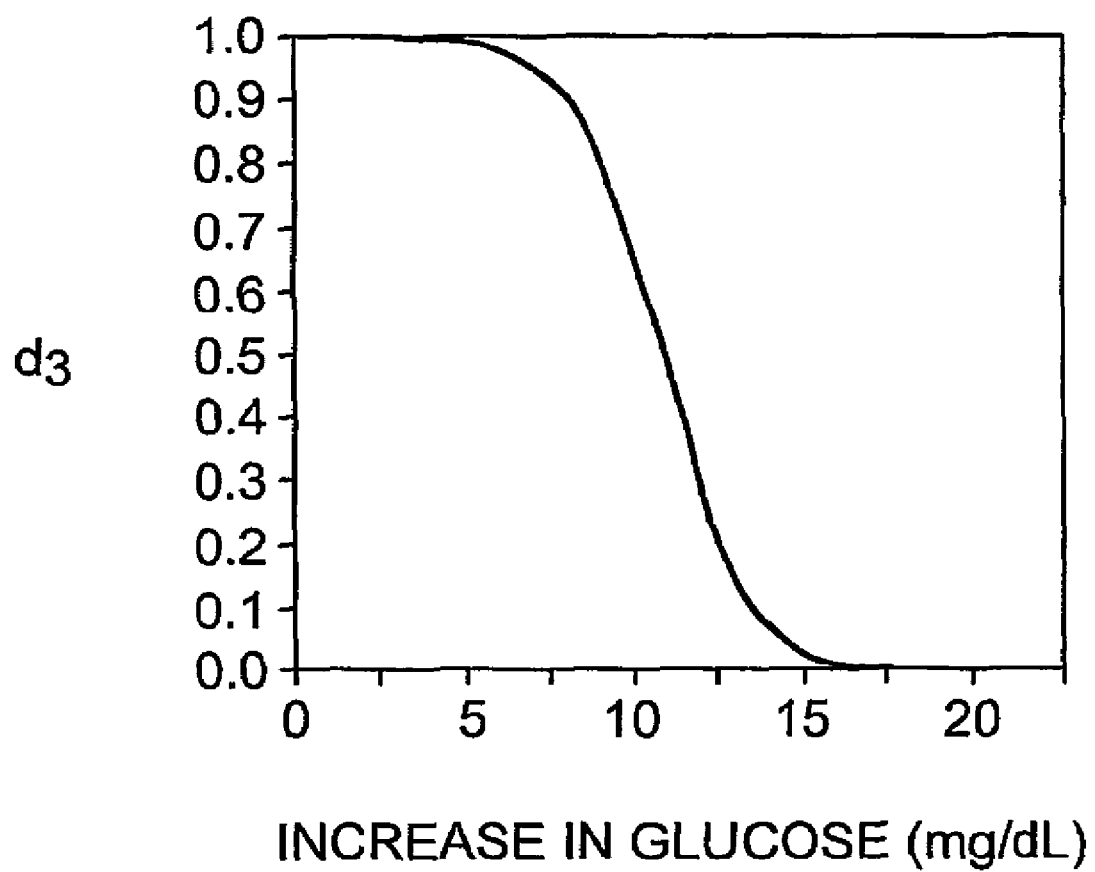

A desirability function was defined for each of the three responses, DBP, CHO, and GLU. The three functions, d1-d3 (FIGS. 5A-5C), were combined into an overall unweighted composite desirability function, $D=(d_1*d_2*d_3)^{1/3}$. The Nelder-Mead simplex procedure was used to carry out the within-patient titration using the composite desirability. The Nelder-Mead algorithm is run on a continuous scale to maintain the flexibility allowed by simplexes of differing shapes. Therefore, at each step, to determine the next dose combination, the doses output by the algorithm are rounded to the nearest whole dose unit. As discussed, it is also possible to round down to the nearest integer value.

For each subject, the starting dose for the initial simplex was chosen to be the same as the smallest combination dose used in the original study: 6.25 mg (2 pills) of HCTZ and 60 mg (4 pills) of DLTZ. The initial step size was chosen to be this initial dose combination increased by 6 pills in the HCTZ axis and by 8 pills in the DLTZ axis. In order to simulate subject responses more realistically, a mixed effects model with a first order autoregressive covariance structure was used. Let $yij=xij'\beta+\epsilon ij$, where yij represents the jth response from the ith subject, $xij=[1\ xi1\ Xi2\ Xi1^2\ Xi2^2\ Xi1\ Xi2]$ represents the 6×1 vector of doses and dose functions for the ith subject at the jth time point, β represents the 6×1 ve xi1 xi2 ctor of parameters taken from the study, and єij represents the random error. The covariance between two observations w time intervals apart on the same subject is $\sigma\epsilon^2\rho^w$, where ρ is the correlation between adjacent observations within the same subject, and w is the number of time intervals between the observations. For this study, the root MSE for DBP, $\sigma_{DBP}$, was 6.2 mm Hg, and 0.35 mmol/L was used for both CHO, $\sigma_{CHO}$, and GLU, $\sigma_{GLU}$.

Figure 6A:
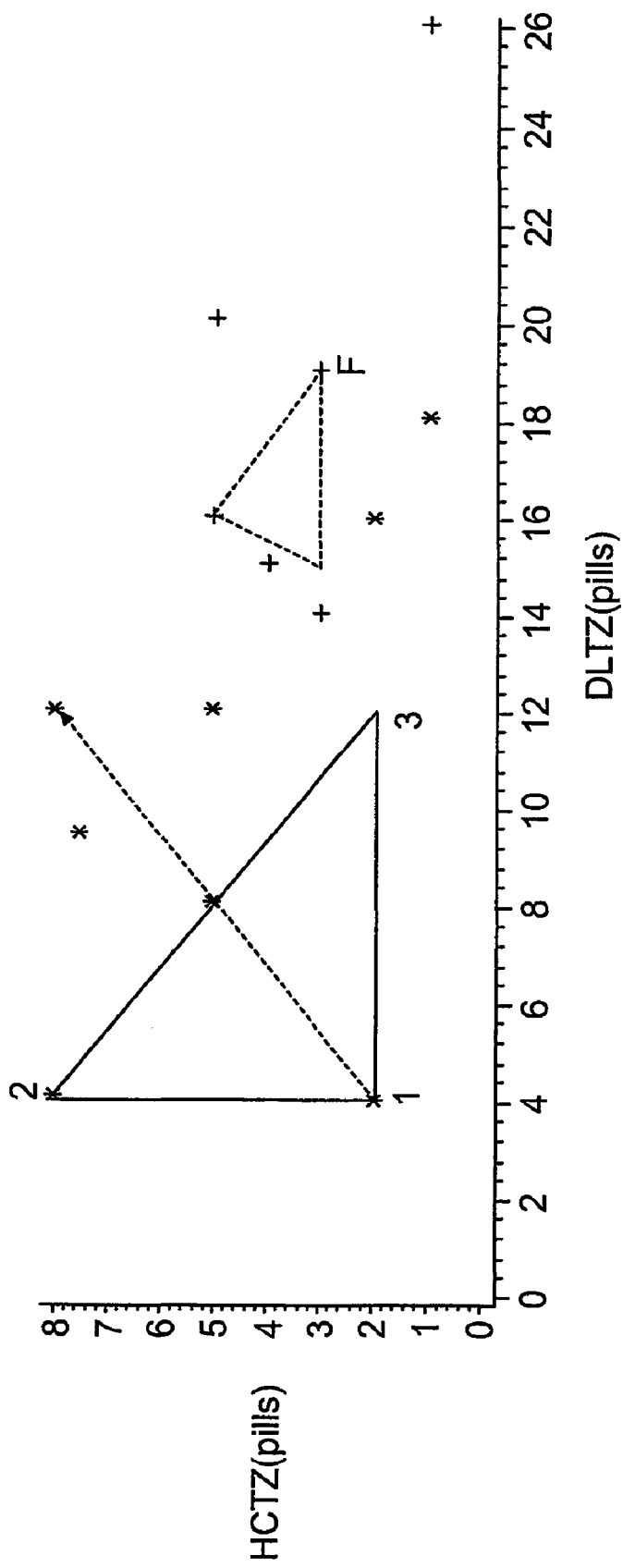
FIGS. 6A and B: A, Simplex movement for one subject in a two-dimensional dose space. The subject is evaluated at each of three initial dose combinations (1,2,3) [2 pills HCTZ/4 pills DLTZ; 8 pills/4 pills; and 2 pills/12 pills]. The simplex reflects away from the combination producing the least desirable response (in this example, point 1). The final optimized dose combination (F) after 20 steps is 3 pills HCTZ and 19 pills DLTZ, corresponding to a simulated decrease in diastolic blood pressure of 18.4 mmHg B, Simplex movement for one subject in a two-dimensional dose space with smaller initial steps. The subject is evaluated at each of three initial dose combinations (1,2,3) similarly to above, but the initial simplex is smaller [2 pills HCTZ/4 pills DLTZ; 6 pills/4 pills; and 2 pills/10 pills]. Note that the process ends with a combination similar to that reached above, 3 pills HCTZ and 18 pills DLTZ, corresponding to a simulated decrease in diastolic blood pressure of 15.7 mmHg.
Figure 6B:
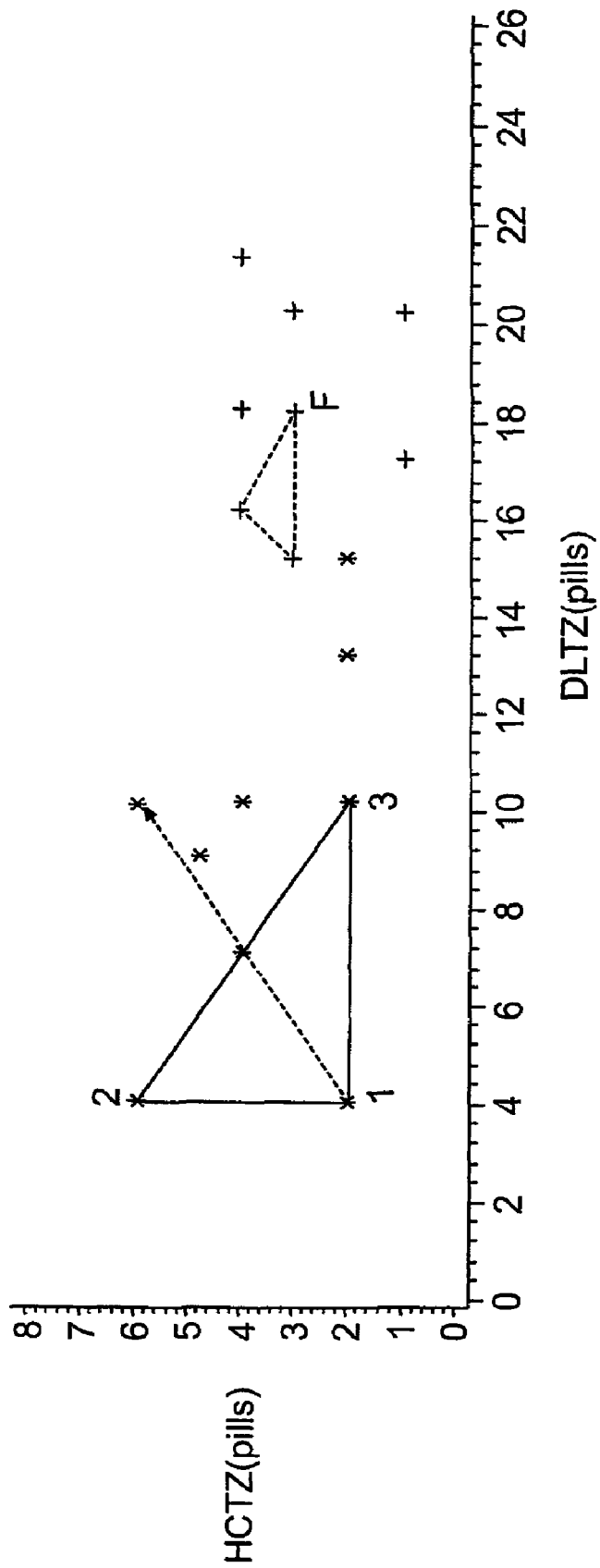

The simulated response at each vertex of the simplex was obtained in triplicate and the responses were averaged. The desirability for each averaged response was compared, and the location of the next dose combination to be given was determined by the Nelder-Mead algorithm, rounding to the nearest whole pill. FIG. 6A is an example showing the simplex movement for a single subject. The titration was continued for 20 steps. At the last step, the final simplex was evaluated and the dose combination associated with the most desirable response was taken as the final treatment combination. This subject arrived at a final dose combination of 3 pills HCTZ and 19 pills DLTZ, with a simulated decrease in DBP of 18.4mmHg. FIG. 6B demonstrates the simplex movement for the same subject starting with a smaller initial step size increase of 4 pills in the HCTZ axis and 6 pills in the DLTZ axis, with titration continuing for 20 steps. The final dose combination reached was 3 pills of HCTZ and 18 pills of DLTZ, similar to that obtained with the larger step size. The corresponding decrease in DBP was 15.7mmHg.

Figure 7:
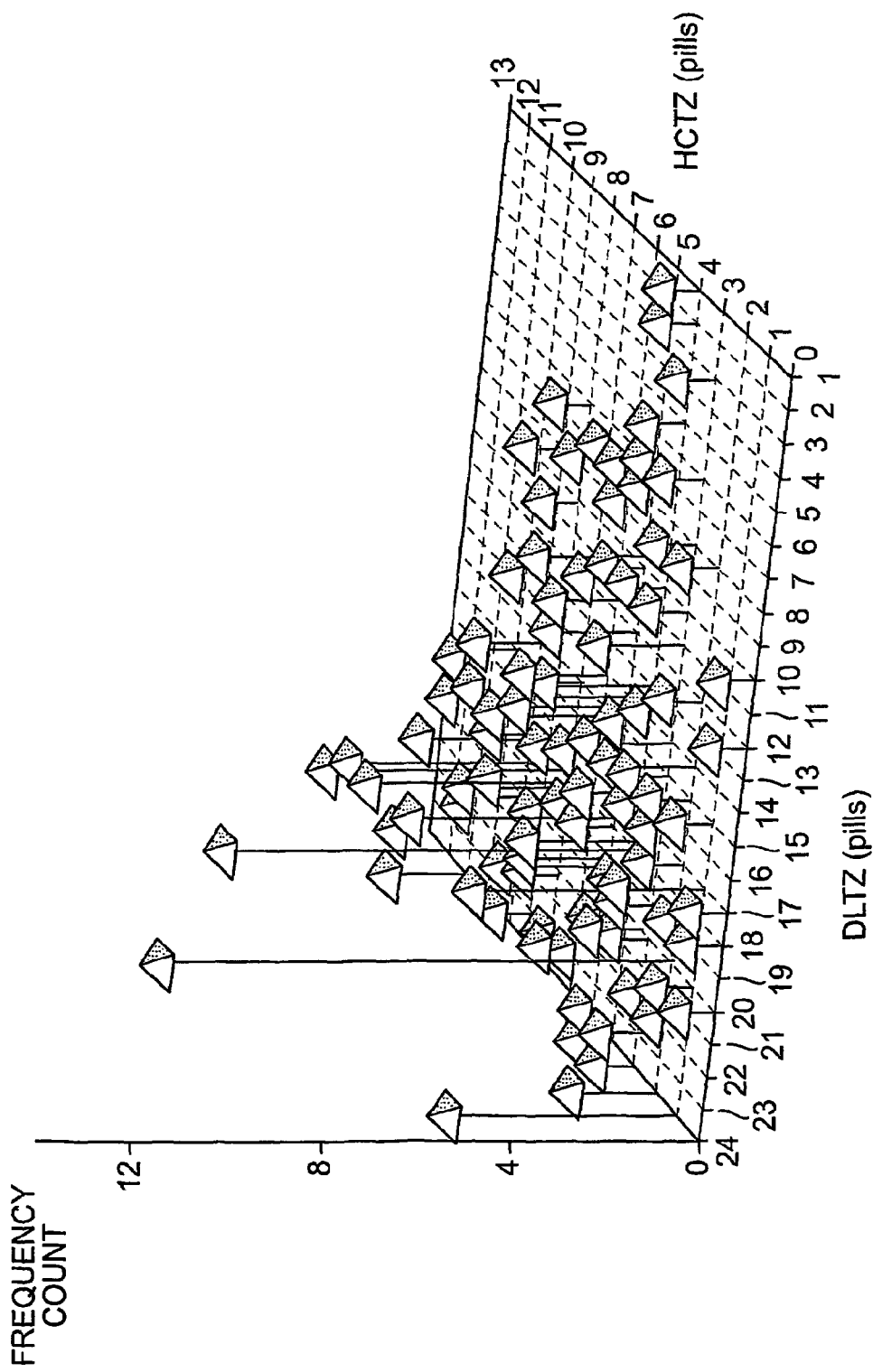
FIG. 7: Pyramid plot of final dose locations for a simulated group of 175 subjects who have completed the 16 steps of titration, using a correlation of 0.7. In this simulation, the desirability function for DBP shown in FIG. 5 was used to target a reduction in diastolic blood pressure (DBP). The mean decrease in DBP was 17.7 mmHg. The mean final dose combination was 4.6 pills HCTZ and 16.2 pills DLTZ.
Figure 8A:
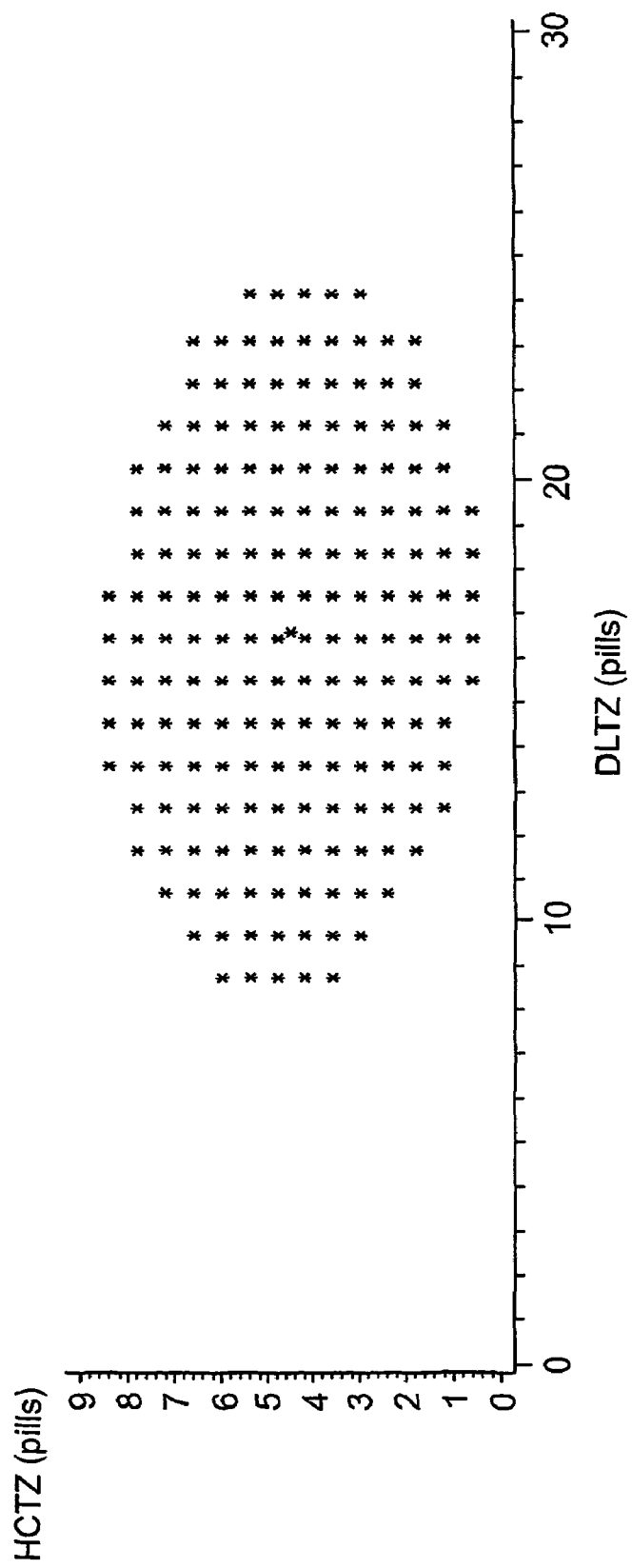
FIGS. 8A and B: A, Asymptotic confidence ellipsoid based on the Wilcoxon signed rank statistic. A group of 175 subjects was simulated using the desirability function for DBP in FIG. 5. B, Asymptotic confidence ellipsoid based on the mean. A group of 175 subjects was simulated using the desirability function for DBP in FIG. 5.
Figure 8B:
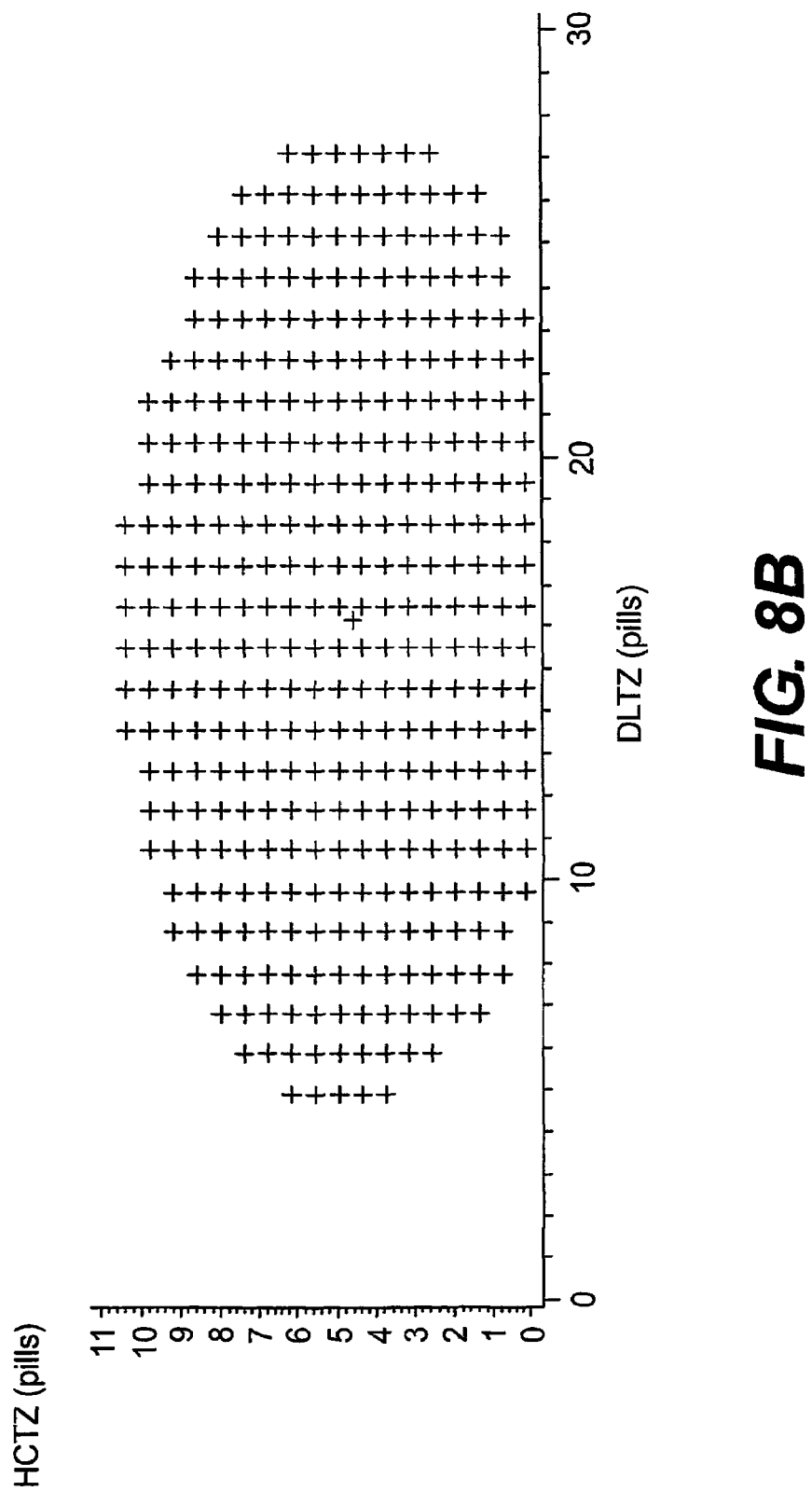

FIG. 7 demonstrates the final dose locations for a simulated group of 175 subjects who have completed the titration process, and FIG. 8A shows the asymptotic confidence ellipsoid about the central location estimate for the Wilcoxon Signed Rank statistic and FIG. 8B shows the confidence ellipsoid about the mean. A correlation between successive blood pressure observations of $\rho=0.7$ was used and the process continued for 16 steps.

For the main simulation study, five groups of 100 simulations were run using sample sizes of N=175 with 16 and 32 steps. The simulations were run first using the desirability function for DBP alone, d4 (FIG. 5), and then repeated using the composite desirability function, $D=(d1*d2*d3)^{1/3}$, which took into account serum cholesterol and serum glucose measurements in addition to the DBP. Additionally, to examine the effect of the correlation between successive observations, $\rho$, the correlation was varied from 0.1 to 0.8. In the simulations with the composite desirability function, the correlation between successive DBP measurements was varied from 0.1 to 0.8, while the correlations for both CHO and GLU were fixed at 0.7.

Number of Steps and Correlation Between Successive Observations within a Patient Using the desirability function for DBP, d4, we see in Table 3 that the proportion of subjects showing improvement over the baseline was 1 (i.e. 100%) for all cases, using either the Fisher Sign test or the Wilcoxon Signed Rank test. All subjects also showed improvement when the final response was compared to the simulated response to single drug treatment with 25 mg of HCTZ, the highest dose used in the study. A similar result was seen in comparing the response to treatment with a 180 mg dose of DLTZ. The mean decrease in DBP, shown in the far right column, did not appear to change as the number of steps was increased from 16 to 32. However, the size of the reduction in DBP did appear to increase as the correlation increased. Table 4 shows the percentage of confidence ellipsoids which included the origin, included the hydrochlorothiazide axis only, included the diltiazem axis only, or included both axes, also using the desirability for DBP alone. The final central dose locations for diltiazem and hydrochlorothiazide are also given in the far right columns, using both the mean and the Wilcoxon Signed Rank statistics as measures of central location. Using Mardia's test, in many instances the multivariate distribution of the final dose locations for each simulation showed some departure from normality, suggesting the nonparametric approach to be most appropriate. As the correlation was increased from 0.1 to 0.8, the simplex appeared to move further up the DLTZ axis, resulting in a higher final dose of DLTZ and a tighter confidence ellipsoid. Increasing the number of steps from 16 to 32 did not appear to have much effect, suggesting that the simplex had already arrived at a final dose after 16 steps.

TABLE 3

Proportion of improved responses using the Fisher sign test or Wilcoxon signed-rank test. Simulations were done using the desirability function for diastolic blood pressure alone (d1). The mean decrease in DBP is shown in the far right column.

| N | Steps | ρ | | Baseline | DLTZ Alone | HCTZ Alone | Decrease in DBP (mmHg) |
|---|---|---|---|---|---|---|---|
| 175 | 16 | 0.1 | Fisher (SE) | 1(0) | 1(0) | 1(0) | 16.4 |
| | | | Wilc(SE) | 1(0) | 1(0) | 1(0) | |
| | | 0.3 | Fisher (SE) | 1(0) | 1(0) | 1(0) | 16.8 |
| | | | Wilc(SE) | 1(0) | 1(0) | 1(0) | |
| | | 0.5 | Fisher (SE) | 1(0) | 1(0) | 1(0) | 16.9 |
| | | | Wilc(SE) | 1(0) | 1(0) | 1(0) | |
| | | 0.7 | Fisher (SE) | 1(0) | 1(0) | 1(0) | 17.7 |
| | | | Wilc(SE) | 1(0) | 1(0) | 1(0) | |
| | | 0.8 | Fisher (SE) | 1(0) | 1(0) | 1(0) | 18.6 |
| | | | Wilc(SE) | 1(0) | 1(0) | 1(0) | |
| | 32 | 0.1 | Fisher (SE) | 1(0) | 1(0) | 1(0) | 16.3 |
| | | | Wilc(SE) | 1(0) | 1(0) | 1(0) | |
| | | 0.3 | Fisher (SE) | 1(0) | 1(0) | 1(0) | 16.9 |
| | | | Wilc(SE) | 1(0) | 1(0) | 1(0) | |
| | | 0.5 | Fisher (SE) | 1(0) | 1(0) | 1(0) | 17.1 |
| | | | Wilc(SE) | 1(0) | 1(0) | 1(0) | |
| | | 0.7 | Fisher (SE) | 1(0) | 1(0) | 1(0) | 18.2 |
| | | | Wilc(SE) | 1(0) | 1(0) | 1(0) | |
| | | 0.8 | Fisher (SE) | 1(0) | 1(0) | 1(0) | 18.6 |
| | | | Wilc(SE) | 1(0) | 1(0) | 1(0) | |

TABLE 4

Evaluation of the confidence ellipsoids using a parametric and nonparametric approach. Simulations were done using the desirability function for diastolic blood pressure alone (d1). The columns show the percentage of confidence ellipsoids containing the origin, containing the HCTZ axis only, containing the DLTZ axis only, or containing both axes. The rightmost columns show the final dose locations for HCTZ and DLTZ using either the mean or Wilcoxon signed-rank statistic as the measure of central location.

| N | Steps | ρ | | Origin | DLTZ Axis Only | HCTZ Axis Only | Both Axes | Final Dose HCTZ | Final Dose DLTZ |
|---|---|---|---|---|---|---|---|---|---|
| 175 | 16 | 0.1 | Mean | 0 | | 0 | 97.2 | 2.8 | 4.5 | 14.0 |
| | | | (SE) | | | | (1.30) | (130) | (0.03) | (0.02) |
| | | | Wilc | | 1.6 | 13.4 | 39.0 | 23.2 | 4.4 | 14.2 |
| | | | (SE) | | (1.52) | (2.92) | (2.92) | (4.97) | (0.03) | (0.03) |
| | | 0.3 | Mean | 0 | | 0 | 99.6 | 0.4 | 4.5 | 14.5 |
| | | | (SE) | | | | (0.89) | (0.89) | 0.02) | (0.01) |
| | | | Wilc | 0.8(0.45) | | 9.6(2.70) | 43.4 | 16.2 | 4.4 | 14.7 |
| | | | (SE) | | | | (4.22) | (3.27) | (0.03) | (0.01) |

TABLE 4-continued

Evaluation of the confidence ellipsoids using a parametric and nonparametric approach. Simulations were done using the desirability function for diastolic blood pressure alone (d1). The columns show the percentage of confidence ellipsoids containing the origin, containing the HCTZ axis only, containing the DLTZ axis only, or containing both axes. The rightmost columns show the final dose locations for HCTZ and DLTZ using either the mean or Wilcoxon signed-rank statistic as the measure of central location.

| N | Steps | ρ | | Origin | DLTZ Axis Only | HCTZ Axis Only | Both Axes | Final Dose HCTZ | Final Dose DLTZ |
|---|---|---|---|---|---|---|---|---|---|
| | | 0.5 | Mean | 0 | 0 | 100 | 0 | 4.5 | 15.2 |
| | | | (SE) | | | | | (0.02) | (0.02) |
| | | | Wilc | 0 | 4.8(1.92) | 51.2 | 8.2 | 4.4 | 15.5 |
| | | | (SE) | | | (5.12) | (2.17) | (0.02) | (0.03) |
| | | 0.7 | Mean | 0 | 0 | 100 | 0 | 4.6 | 16.2 |
| | | | (SE) | | | | | (0.02) | (0.02) |
| | | | Wilc | 0 | 0.4(0.89) | 64.6 | 0.4 | 4.5 | 16.6 |
| | | | (SE) | | | (5.50) | (0.89) | (0.02) | (0.03) |
| | | 0.8 | Mean | 0 | 0 | 100 | 0 | 4.6 | 17.1 |
| | | | (SE) | | | | | (0.02) | (0.02) |
| | | | Wilc | 0 | 0 | 68.0 | 0 | 4.5 | 17.3 |
| | | | (SE) | | | (3.94) | | (0.03) | (0.03) |
| 32 | | 0.1 | Mean | 0 | 0 | 99.4 | 0.6 | 4.4 | 14.2 |
| | | | (SE) | | | (0.55) | (0.55) | (0.01) | (0.05) |
| | | | Wilc | 0.6(0.55) | 10.8(4.87) | 49.4 | 21.8 | 4.2 | 14.4 |
| | | | (SE) | | | (4.10) | (4.44) | (0.02) | (0.05) |
| | | 0.3 | Mean | 0 | 0 | 100 | 0 | 4.4 | 14.7 |
| | | | (SE) | | | | | (0.01) | (0.06) |
| | | | Wilc | 0.2(0.45) | 8.2(0.84) | 54.0 | 17.6 | 4.3 | 15.0 |
| | | | (SE) | | | (3.87) | (2.30) | (0.02) | (0.07) |
| | | 0.5 | Mean | 0 | 0 | 100 | 0 | 4.4 | 15.3 |
| | | | (SE) | | | | | (0.02) | (0.03) |
| | | | Wilc | 0 | 2.6(1.14) | 61.4 | 5.60 | 4.3 | 15.7 |
| | | | (SE) | | | (8.88) | (1.95) | (0.02) | (0.02) |
| | | 0.7 | Mean | 0 | 0 | 100 | 0 | 4.5 | 16.4 |
| | | | (SE) | | | | | (0.02) | (0.01) |
| | | | Wilc | 0 | 0 | 71.0 | 0 | 4.4 | 16.7 |
| | | | (SE) | | | (3.87) | | (0.02) | (0.02) |
| | | 0.8 | Mean | 0 | 0 | 100 | 0 | 4.5 | 17.1 |
| | | | (SE) | | | | | (0.004) | (0.04) |
| | | | Wilc | 0 | 0 | 75.4 | 0 | 4.4 | 17.4 |
| | | | (SE) | | | (2.30) | | (0.01) | (0.05) |

The simulations were then repeated using the composite desirability function, D, which combined the main outcome of interest, diastolic blood pressure, with two other endpoints which the study authors reported on, serum glucose and serum cholesterol. In these simulations, the correlation between successive DBP measurements within a patient was increased from 0.1 to 0.8, while the correlations for both CHO and GLU were fixed at 0.7. Tables 5 and 6, show that the simplex does not move as far along the HCTZ axis or DLTZ axis when these other endpoints are taken into consideration, indicating that one or both of these endpoints are acting as constraints. However, from Table 5.3, we see that even at these doses, there is still a significant improvement in the response for all subjects in all cases.

TABLE 5

Proportion of improved responses using the Fisher sign test or Wilcoxon signed-rank test. Simulations were done using the composite desirability function (D). The correlation between successive DBP measurements was varied from 0.1 to 0.8, while the correlations for both CHO and GLU were fixed at 0.7. The rightmost columns show the mean decrease in diastolic blood pressure, the mean change in cholesterol and the mean change in serum glucose.

| N | Steps | ρ | | Baseline | DLTZ Alone | HCTZ Alone | Decrease in DBP (mmHg) | Change in Chol (mmol/L) | Change in Glu (mmol/L) |
|---|---|---|---|---|---|---|---|---|---|
| 175 | 16 | 0.1 | Fisher(SE) | 1(0) | 1(0) | 1(0) | 11.9 | 0.24 | 0.29 |
| | | | Wilc(SE) | 1(0) | 1(0) | 1(0) | | | |
| | | 0.3 | Fisher(SE) | 1(0) | 1(0) | 1(0) | 11.9 | 0.25 | 0.29 |
| | | | Wilc(SE) | 1(0) | 1(0) | 1(0) | | | |

TABLE 5-continued

Proportion of improved responses using the Fisher sign test or Wilcoxon signed-rank test. Simulations were done using the composite desirability function (D). The correlation between successive DBP measurements was varied from 0.1 to 0.8, while the correlations for both CHO and GLU were fixed at 0.7. The rightmost columns show the mean decrease in diastolic blood pressure, the mean change in cholesterol and the mean change in serum glucose.

| N | Steps | $\rho$ | | Baseline | DLTZ Alone | HCTZ Alone | Decrease in DBP (mmHg) | Change in Chol (mmol/L) | Change in Glu (mmol/L) |
|---|---|---|---|---|---|---|---|---|---|
| | | 0.5 | Fisher(SE) | 1(0) | 1(0) | 1(0) | 11.9 | 0.25 | 0.31 |
| | | | Wilc(SE) | 1(0) | 1(0) | 1(0) | | | |
| | | 0.7 | Fisher(SE) | 1(0) | 1(0) | 1(0) | 12.0 | 0.24 | 0.29 |
| | | | Wilc(SE) | 1(0) | 1(0) | 1(0) | | | |
| | | 0.8 | Fisher(SE) | 1(0) | 1(0) | 1(0) | 12.1 | 0.24 | 0.27 |
| | | | Wilc(SE) | 1(0) | 1(0) | 1(0) | | | |
| | 32 | 0.1 | Fisher(SE) | 1(0) | 1(0) | 1(0) | 11.3 | 0.25 | 0.27 |
| | | | Wilc(SE) | 1(0) | 1(0) | 1(0) | | | |
| | | 0.3 | Fisher(SE) | 1(0) | 1(0) | 1(0) | 11.3 | 0.27 | 0.26 |
| | | | Wilc(SE) | 1(0) | 1(0) | 1(0) | | | |
| | | 0.5 | Fisher(SE) | 1(0) | 1(0) | 1(0) | 11.6 | 0.25 | 0.31 |
| | | | Wilc(SE) | 1(0) | 1(0) | 1(0) | | | |
| | | 0.7 | Fisher(SE) | 1(0) | 1(0) | 1(0) | 11.9 | 0.24 | 0.27 |
| | | | Wilc(SE) | 1(0) | 1(0) | 1(0) | | | |
| | | 0.8 | Fisher(SE) | 1(0) | 1(0) | 1(0) | 11.8 | 0.23 | 0.27 |
| | | | Wilc(SE) | 1(0) | 1(0) | 1(0) | | | |

TABLE 6

Evaluation of the confidence ellipsoids using a parametric and nonparametric approach. Simulations were done using the composite desirability function (D). The correlation between successive DBP measurements was varied from 0.1 to 0.8, while the correlations for both CHO and GLU were fixed at 0.7. The columns show the percentage of confidence ellipsoids (SE) containing the origin, containing the HCTZ axis only, containing the DLTZ axis only, or containing both axes. The rightmost columns show the final dose locations for HCTZ and DLTZ using either the mean or Wilcoxon signed-rank statistic as the measure of central location.

| N | Steps | $\rho$ | | Origin | DLTZ Axis Only | HCTZ Axis Only | Both Axes | Final Dose HCTZ | Final Dose DLTZ |
|---|---|---|---|---|---|---|---|---|---|
| 175 | 16 | 0.1 | Mean(SE) | 0 | 0 | 34.0 (5.70) | 66.0 (5.70) | 3.1 (0.02) | 9.2 (0.02) |
| | | | Wilc(SE) | 9.0(1.41) | 0 | 61.4 (2.07) | 38.6 (2.07) | 3.0 (0.02) | 9.2 (0.02) |
| | | 0.3 | Mean(SE) | 0 | 0 | 35.6 (3.05) | 64.4 (3.05) | 3.1 (0.02) | 9.2 (0.02) |
| | | | Wilc (SE) | 8.8(4.92) | 0 | 60.8 (4.32) | 39.2 (4.32) | 3.0 (0.02) | 9.3 (0.03) |
| | | 0.5 | Mean(SE) | 0 | 0 | 38.2 (4.44) | 61.8 (4.44) | 3.1 (0.02) | 9.3 (0.02) |
| | | | Wilc (SE) | 9.8(2.28) | 0 | 61.4 (2.70) | 38.6 (2.70) | 3.0 (0.02) | 9.4 (0.02) |
| | | 0.7 | Mean(SE) | 0 | 0 | 44.0 (5.24) | 56.0 (5.24) | 3.1 (0.02) | 9.4 (0.02) |
| | | | Wilc(SE) | 8.8(3.27) | 0 | 61.4 (5.77) | 38.6 (5.77) | 3.0 (0.01) | 9.5 (0.02) |
| | | 0.8 | Mean(SE) | 0 | 0 | 51.4 (3.58) | 48.6 (3.58) | 3.1 (0.02) | 9.5 (0.02) |
| | | | Wilc (SE) | 9.2(2.17) | 0 | 59.8 (4.21) | 40.2 (4.21) | 3.0 (0.02) | 9.6 (0.03) |
| | 32 | 0.1 | Mean(SE) | 0 | 0 | 36.4 (3.71) | 63.6 (3.71) | 3.0 (0.02) | 9.2 (0.03) |
| | | | Wilc(SE) | 9.2(1.64) | 0 | 59.2 (5.26) | 40.8 (5.26) | 2.8 (0.03) | 9.3 (0.03) |
| | | 0.3 | Mean(SE) | 0 | 0 | 38.6 (3.78) | 61.4 (3.78) | 3.0 (0.02) | 9.2 (0.04) |
| | | | Wilc (SE) | 6.4(1.67) | 0 | 56.4 (3.13) | 43.6 (3.13) | 2.8 (0.02) | 9.3 (0.04) |

TABLE 6-continued

Evaluation of the confidence ellipsoids using a parametric and nonparametric approach. Simulations were done using the composite desirability function (D). The correlation between successive DBP measurements was varied from 0.1 to 0.8, while the correlations for both CHO and GLU were fixed at 0.7. The columns show the percentage of confidence ellipsoids (SE) containing the origin, containing the HCTZ axis only, containing the DLTZ axis only, or containing both axes. The rightmost columns show the final dose locations for HCTZ and DLTZ using either the mean or Wilcoxon signed-rank statistic as the measure of central location.

| N | Steps | $\rho$ | | Origin | DLTZ Axis Only | HCTZ Axis Only | Both Axes | Final Dose HCTZ | Final Dose DLTZ |
|---|---|---|---|---|---|---|---|---|---|
| | | 0.5 | Mean(SE) | 0 | 0 | 40.8 (3.56) | 59.2 (3.96) | 3.0 (0.01) | 9.3 (0.05) |
| | | | Wilc (SE) | 5.2(2.05) | 0 | 55.0 (3.39) | 45.0 (3.39) | 2.8 (0.01) | 9.4 (0.05) |
| | | 0.7 | Mean(SE) | 0 | 0 | 48.6 (4.16) | 51.4 (4.16) | 2.9 (0.01) | 9.4 (0.03) |
| | | | Wilc (SE) | 7.0(2.55) | 0 | 59.4 (2.07) | 40.6 (2.07) | 2.8 (0.02) | 9.5 (0.03) |
| | | 0.8 | Mean(SE) | 0 | 0 | 54.2 (1.92) | 45.8 (1.92) | 2.9 (0.01) | 9.5 (0.04) |
| | | | Wilc (SE) | 6.8(2.17) | 0 | 53.0 (3.54) | 47.0 (3.45) | 2.8 (0.02) | 9.6 (0.04) |

Initial Step Size

Tables 7 and 8 show the results of changing the initial step size from an increase of 6 pills in the HCTZ axis and 8 pills in the DLTZ axis, to an increase of only 5 pills/7 pills, or 4 pills/6 pills over the initial dose combination. After 16 steps, using the desirability function for DBP, a correlation of 0.7, and a sample size of 175, there was a slightly smaller decrease in the DBP response. In addition, the final dose combinations also decreased as the initial step size became smaller. This would suggest that either the simplex has not had enough time to reach the same improved dose as with the larger step size, or perhaps the simplex has reached a plateau and the variability is too large for it to move further along the dose response surface.

TABLE 7

A comparison of initial step sizes. Simulations were done using the desirability function for diastolic blood pressure alone (d1), with 16 steps, $\rho = 0.7$. The table shows the proportion of improved responses using the Fisher sign test or the Wilcoxon signed-rank test. The effect of decreasing the initial step size is shown, with the mean decrease in diastolic blood pressure given in the rightmost column.

| Step Size (Pills) | | Baseline | DLTZ Alone | HCTZ Alone | Decrease in DBP (mmHg) |
|---|---|---|---|---|---|
| +4 | Fisher (SE) | 1(0) | 1(0) | 1(0) | 17.7 |
| | Wilc (SE) | 1(0) | 1(0) | 1(0) | |
| +3 | Fisher (SE) | 1(0) | 1(0) | 1(0) | 16.7 |
| | Wilc (SE) | 1(0) | 1(0) | 1(0) | |
| +2 | Fisher (SE) | 1(0) | 1(0) | 1(0) | 16.5 |
| | Wilc (SE) | 1(0) | 1(0) | 1(0) | |

TABLE 8

A comparison of initial step sizes. Simulations were done using the desirability function for diastolic blood pressure alone (d1), with 16 steps, $\rho = 0.7$. The columns show the percentage of confidence ellipsoids (SE) containing the origin, containing the HCTZ axis only, containing the DLTZ axis only, or containing both axes. The effect of decreasing the initial step size is shown, with the rightmost columns giving the final dose locations for HCTZ and DLTZ using either the mean or Wilcoxon signed-rank statistic as the measure of central location.

| Step size (Pills) | | Origin | DLTZ Axis Only | HCTZ Axis Only | Both Axes | Final Dose HCTZ | Final Dose DLTZ |
|---|---|---|---|---|---|---|---|
| +4 | Mean (SE) | 0 | 0 | 100 | 0 | 4.6 (0.02) | 16.2 (0.02) |
| | Wilc (SE) | 0 | 0.4 (0.89) | 64.6 (5.50) | 0.4 (0.89) | 4.5 (0.02) | 16.6 (0.03) |
| +3 | Mean (SE) | 0 | 0 | 100 | 0 | 4.5 (0.01) | 15.2 (0.05) |
| | Wilc (SE) | 0 | 6.8 (2.59) | 55.4 (5.18) | 16.0 (4.18) | 4.4 (0.02) | 15.5 (0.06) |
| +2 | Mean (SE) | 0 | 0 | 90.4 (1.95) | 9.6 (1.95) | 4.2 (0.02) | 13.7 (0.04) |
| | Wilc (SE) | 4.2 (2.77) | 7.4 (2.61) | 49.2 (2.59) | 30.4 (4.62) | 4.1 (0.02) | 13.9 (0.04) |

Sample Size

Tables 9 and 10 display the results of changes to the sample size. Simulations were run with sample sizes of 25, 50, 175, and 300 subjects, using the desirability function for DBP alone. The between-observations correlation was fixed at 0.7, and the titration was continued for 16 steps. In general, changes to the sample size did not appear to significantly affect the outcomes. In Table 9, the decrease in the DBP remains similar across cases and there is a significant improvement in the response for all cases. In Table 10, the final dose combinations also remain similar across the cases.

TABLE 9

Sample size comparison. Simulations were done using the desirability function for diastolic blood pressure alone (d1), with 16 steps, $\rho = 0.7$. The table shows the proportion of improved responses using the Fisher sign test or the Wilcoxon signed-rank test. The effect of increasing the sample size is shown, with the mean decrease in diastolic blood pressure given in the rightmost column.

| Sample Size | | Baseline | DLTZ Alone | HCTZ Alone | Decrease in DBP (mmHg) |
|---|---|---|---|---|---|
| 25 | Fisher (SE) | 1(0) | 1(0) | 1(0) | 18.2 |
|    | Wilc (SE)   | 1(0) | 1(0) | 1(0) |      |
| 50 | Fisher (SE) | 1(0) | 1(0) | 1(0) | 16.6 |
|    | Wilc (SE)   | 1(0) | 1(0) | 1(0) |      |
| 175 | Fisher (SE)| 1(0) | 1(0) | 1(0) | 17.7 |
|    | Wilc (SE)   | 1(0) | 1(0) | 1(0) |      |
| 300 | Fisher (SE)| 1(0) | 1(0) | 1(0) | 17.7 |
|    | Wilc (SE)   | 1(0) | 1(0) | 1(0) |      |

TABLE 10

Sample size comparison. Simulations were done using the desirability function for diastolic blood pressure alone (d1), with 16 steps, $\rho = 0.7$. The columns show the percentage of confidence ellipsoids (SE) containing the origin, containing the HCTZ axis only, containing the DLTZ axis only, or containing both axes. The effect of decreasing the initial step size is shown, with the rightmost columns giving the final dose locations for HCTZ and DLTZ using either the mean or Wilcoxon signed-rank statistic as the measure of central location.

| Sample Size | | Origin | DLTZ Axis Only | HCTZ Axis Only | Both Axes | Final Dose HCTZ | Final Dose DLTZ |
|---|---|---|---|---|---|---|---|
| 25 | Mean | 0.6 | 0 | 95.0 | 3.6 | 4.6 | |
|    | (SE)  | (0.89) |   | (1.87) | (1.52) | (0.04) | |
|    | Wilc  | 0.6 | 0.4 | 91.8 | 3.4 | 4.5 | |
|    | (SE)  | (0.89) | (0.54) | (1.64) | (0.89) | (0.04) | |
| 50 | Mean | 0 | 0 | 99.6 | 0.4 | 4.6 | |
|    | (SE)  |   |   | (0.55) | (0.55) | (0.06) | |
|    | Wilc  | 0 | 0.2 | 84.0 | 1.0 | 4.4 | |
|    | (SE)  |   | (0.45) | (2.24) | (1.22) | (0.06) | |
| 175 | Mean | 0 | 0 | 100 | 0 | 4.6 | |
|    | (SE)  |   |   |   |   | (0.02) | |
|    | Wilc  | 0 | 0.4 | 64.5 | 0.4 | 4.5 | |
|    | (SE)  |   | (0.89) | (5.50) | (0.898) | (0.02) | |
| 300 | Mean | 0 | 0 | 100 | 0 | 4.6 | |
|    | (SE)  |   |   |   |   | (0.06) | |
|    | Wilc  | 0 | 0 | 97.2 | 2.8 | 4.5 | 16.6 |
|    | (SE)  |   |   | (1.10) | (1.10) | (0.01) | (0.01) |

Variation in the Desirability Function

The sensitivity of the titration method to variability in the chosen desirability function was also assessed. To determine whether small modifications in the desirability function had any effect on the resulting dose locations and responses, we ran simulations using three modified desirability functions in addition to $d_4$, the desirability function for DBP, with 16 steps, a correlation of 0.7, and a sample size of 175.

Tables 11 and 12 show that sharpening the peak desirability as with $d_a$, increasing the width of the desirability function as with $d_b$, or decreasing the width and sharpening the peak simultaneously as with $d_c$, did not result in any appreciable change in the outcome with respect to either response or dose location. There was little or no change in the decrease in DBP or final dose combinations, indicating that the process is robust, or relatively insensitive, to small changes in the definition of the desirability function. So while the desirability function has to be defined carefully, there is some room for variation when deciding on the parameters.

TABLE 11

A comparison of desirability functions. The table shows the proportion of improved responses using the Fisher sign test or the Wilcoxon signed-rank test. The parameters for the modified desirability functions are shown, with the mean decrease in diastolic blood pressure given in the rightmost column.

| Dsbl | N = 175 Steps = 16 $\rho = 0.7$ | $(Y_{i^*}, 'Y_i^*')$ | $Y_{i^*}, "Y_i^*")$ | Baseline | DLTZ Alone | HCTZ Alone | Decrease in DBP (mmHg) |
|---|---|---|---|---|---|---|---|
| $d_1$ | Fisher(SE) | (0, 10) | (30, 40) | 1(0) | 1(0) | 1(0) | 17.7 |
|       | Wilc (SE)  |         |          | 1(0) | 1(0) | 1(0) |      |
| $d_2$ | Fisher(SE) | (0, 20) | (20, 40) | 1(0) | 1(0) | 1(0) | 17.5 |
|       | Wilc (SE)  |         |          | 1(0) | 1(0) | 1(0) |      |
| $d_3$ | Fisher(SE) | (−5, 10) | (30, 45) | 1(0) | 1(0) | 1(0) | 17.5 |
|       | Wilc (SE)  |          |          | 1(0) | 1(0) | 1(0) |      |
| $d_4$ | Fisher(SE) | (10, 20) | (20, 30) | 1(0) | 1(0) | 1(0) | 17.5 |
|       | Wilc (SE)  |          |          | 1(0) | 1(0) | 1(0) |      |

TABLE 12

A comparison of desirability functions. The columns show
the percentage of confidence ellipsoids (SE) containing the
origin, containing the HCTZ axis only, containing the DLTZ
axis only, or containing both axes. The parameters for the
modified desirability functions are shown, with the rightmost
columns giving the final dose locations for HCTZ and DLTZ
using either the mean or Wilcoxon signed-rank statistic as
the measure of central location.

| Dsbl | N = 175 Steps = 16 $\rho = 0.7$ | $(Y_{i*}, Y_i^*)$ | $(Y_{i*}, Y_i^*)$ | Origin | DLTZ Axis Only | HCTZ Axis Only | Both Axes | Final Dose HCTZ | Final Dose DLTZ |
|---|---|---|---|---|---|---|---|---|---|
| $d_1$ | Mean (SE) | (0, 10) | (30, 40) | 0 | 0 | 100 | 0 | 4.6 (0.02) | 16.2 (0.02) |
| | Wilc (SE) | | | 0 | 0.4 (0.89) | 64.5 (5.50) | 0.4 (0.89) | 4.5 (0.02) | 16.6 (0.03) |
| $d_2$ | Mean (SE) | (0, 20) | (20, 40) | 0 | 0 | 100 | 0 | 4.6 (0.02) | 16.3 (0.03) |
| | Wilc (SE) | | | 0 | 0.2 (0.45) | 64.0 (3.81) | 0.2 (0.45) | 4.5 (0.02) | 16.6 (0.04) |
| $d_3$ | Mean (SE) | (−5, 10) | (30, 45) | 0 | 0 | 100 | 0 | 4.6 (0.02) | 16.3 (0.02) |
| | Wilc (SE) | | | 0 | 0.4 (0.55) | 66.8 (3.90) | 0.4 (0.89) | 4.4 (0.03) | 16.6 (0.04) |
| $d_4$ | Mean (SE) | (10, 20) | (20, 30) | 0 | 0 | 100 | 0 | 4.6 (0.01) | 16.3 (0.02) |
| | Wilc (SE) | | | 0 | 0.2 (0.45) | 63.6 (3.44) | 0.2 (0.45) | 4.5 (0.02) | 16.6 (0.04) |

From our simulations, it appears that the evolutionary simplex approach is effective in arriving at dose combinations which yield improved responses in patients who are being treated with a combination of multiple therapies, although inferences on the location do not appear to be as sharp as inferences on the response. In comparing the simulation results with the original response data, the final dose locations were found to correspond well with the area of higher response seen in the Burris study (Burris, 1990).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Bell D S, Mayo M S. Outcome of metformin-facilitated reinitiation of oral diabetic therapy in insulin treated patients with non-insulin-dependent diabetes mellitus. *Endocr Pract* 1997;3:73-6.

Berenbaum, M. C. (1990). Direct Search Methods in the Optimisation of Cancer Chemo therapy Regimens. *British Journal of Cancer* 61, 101-9.

Box, M. J. (1958). In Discussion of Experimental Design in Combination Chemotherapy. *Annals of the New York Academy of Sciences* 76, 909-931.

Box, G. E. P., Wilson, K. B. (1951). On the Experimental Attainment of Optimum Conditions. *Journal of the Royal Statistical Society, Series B* 13, 1-45.

Box, M. J. (1965) A new method of constrained optimization and a comparison with other methods. *The Computer Journal*, 8:42-52.

Box, M. J., Davies, D. and Swann, W. H. (1969) *Non-linear Optimization Techniques*, Oliver & Boyd, Edinburgh.

Box, G. E. P., Hunter, J. S. (1959). Condensed Calculations for Evolutionary Operation Programs. *Technometrics* 1, 77-95.

Box, G. E. P., Draper, N. R. (1969). *Evolutionary Operation; a statistical method for process improvement*, John Wiley and Sons, New York.

Box, G. E. P. (1957). Evolutionary Operation: A Method for Increasing Industrial Productivity. *Applied Statistics* 6, 81-101.

Bristol-Myers Squibb. GLUCOVANCE Package Insert. Rev: October 2000.

Burris, J. F., Weir, M. R., Oparil, S., Weber, M., Cady, W. J., Stewart, W. H. (1990). An Assessment of Diltiazem and Hydrochlorothiazide in Hypertension. *Journal of the American Medical Association* 263, 1507-1512.

Carter, W. H., Jr., Wampler, G. L., Stablein, D. M., Campbell, E. D. (1982). Drug Activity as Therapeutic Synergism in Cancer Treatment. *Cancer Research* 42, 2963-2971.

Carter, W. H., Jr., Chinchilli, V. M., Campbell, E. D., Wampler, G. L. (1984). Confidence Interval about the Response at the Stationary Point of a Response Surface, with an Application to Preclinical Cancer Therapy. *Biometrics* 40, 1125-1130.

Centers for Disease Control and Prevention. National Diabetes Fact Sheet: National estimates and general information on diabetes in the United States. Revised edition. Atlanta, Ga.: U.S. Department of Health and Human Services, Centers for Disease Control and Prevention, 1998.

Cox, D. R. (1958). *Planning of Experiments*, John Wiley and Sons, New York.

Cusi, K., DeFronzo, R. A. Metformin: a review of its metabolic effects. *Diabetes Reviews* 1998; 6:89-131.

DeFronzo, R A, Goodman A M. Efficacy of metformin in patients with non-insulin dependent diabetes mellitus. The Multicenter Metformin Study Group. *N Engl J Med* 1995; 333:541-9.

Derringer, G., Suich, R. (1980). Simultaneous Optimization of Several Response Variables. *Journal of Quality Technology* 25, 199-204.

Derringer, G. (1994). A balancing act: optimizing a product's properties. *Quality Progress* 27(6), 51-58.

Ertel N H. Newer therapeutic agents for type 2 diabetes. In: Managing type 2 diabetes: A Postgraduate Medicine Special Report 1997; 25-32.

Fisher, R. A. (1925). *Statistical Methods for Research Workers*, 1st ed. Oliver & Boyd, Edinburgh.

Fisher, R. A. (1935). *The Design of Experiments*, Collier Macmillan, London.

Friedman, M., Savage, L. J. (1947). *Techniques of Statistical Analysis, Chapter* 13, edited by C. Eisenhart, M. W. Hastay, W. A. Wallis, McGraw-Hill, New York.

Gibb, R. D. (1998). Optimal Treatment Combination Estimation for Univariate and Multivariate Response Surface Applications. Ph.D. Dissertation, Department of Biostatistics, Medical College of Virginia, Virginia Commonwealth University, Richmond, Va.

Harrington, E. C. (1965). The desirability function. *Industrial Quality Control* 21, 494-498.

Hermann L S, Scherstén B, Bitzen P O, Kjellstrom T, Lindgarde F, Melander A. Therapeutic comparison of metformin and sulfonylurea, alone and in various combinations. A double-blind controlled study. *Diabetes Care* 1994;17:1100-9.

Hettmansperger, T. P. (1984). *Statistical Inference Based on Ranks*, John Wiley and Sons, Inc., New York.

Hettmansperger, T. P., McKean, J. W. (1998). *Robust Nonparametric Statistical Methods*, John Wiley and Sons, New York.

Hodges, J. L., Lehmann, E. L. (1963). Estimates of Location Based on Rank. *Annals of Mathematical Statistics* 34, 598-611.

Hollander, M., Wolfe, D. A. (1973). *Nonparametric Statistical Methods*, John Wiley and Sons, Inc., New York.

Hotelling, H. (1941). *Annals of Mathematical Statistics* 12, 20.

Hunter, W. G., Kittrell, J. R. (1966). Evolutionary Operation: a Review. *Technometrics* 8, 389-397.

Lebovitz H E. Oral antidiabetic agents: the emergence of alpha-glucosidase inhibitors. *Drugs* 1992;44(Suppl 3):21-8.

Lebovitz H E. Stepwise and combination drug therapy for the treatment of NIDDM. *Diabetes Care* 1994;17:1-3.

Lebovitz H E. Rationale in the management of non-insulin-dependent diabetes. In: Leslie R D, Robbins D C, eds. *Diabetes: clinical science in practice*. New York: Cambridge University Press, 1995:450-64.

Lehmann, E. L. (1975). *Nonparametrics: Statistical Methods Based on Ranks*. Holden-Day, San Francisco.

Mantel, N. (1974). Therapeutic Synergism. *Cancer Chemother. Rep.* Part II 4, 147-149.

Mardia, K. V. (1974). Applications of some measures of multivariate skewness and kurtosis in testing normality and robustness studies. *Sankhya*, B 36, 115-128.

Medical Letter, Inc. Glyburide/Metformin (Glucovance) for type 2 diabetes. Medical Letter on Drugs and Therapeutics 2000;42:105-6.

Morrison, D. F. (1976). *Multivariate Statistical Methods*, McGraw-Hill, New York.

Nelder, J. A., Mead, R. (1965). A Simplex Method for Function Minimization. *Computer Journal* 7, 308-313.

Olsson, D. M., Nelson, L. S. (1975). The Nelder-Mead Simplex Procedure for Function Minimization. *Technometrics* 17, 45-51.

Olsson, D. M. (1974). A Sequential Program for Solving Minimization Problems. *Journal of Quality Technology* 6, 53-57.

Pharmacologic intervention in: Medical management of type 2 diabetes. 4th ed. Alexandria, Va.: American Diabetes Association, 1998:56-72.

Riddle M C. Tactics for Type II diabetes. Endocrinol Metab Clin North Am 1997;26:659-77.

SAS Institute Inc. (1990). *SAS® Procedures Guide, Version 6, Third Edition*, SAS Institute Inc., Cary, N.C.

Segreti, A. C. (1977). The Design of Sequential Clinical Trials in Combination Chemotherapy. Ph.D. Dissertation, Medical College of Virginia, Virginia Commonwealth University, Richmond, Va.

Snedecor, G. W., Cochran, W. G. (1980). *Statistical Methods*, 7th Ed., Iowa State University Press, Ames.

Spendley, W., Hext, G. R., Himsworth, F. R. (1962). Sequential Application of Simplex Designs in Optimization and EVOP. *Technometrics* 4, 441-461.

The Diabetes Control and Complications Trial Research Group. The effect of intensive treatment of diabetes on the development and progression of long-term complications in insulin-dependent diabetes mellitus. *N Engl J Med* 1993; 329:977-86.

Tukey, J. W. (1949). The simplest signed-rank tests. *Mem. Report* 17, Statistical Research Group, Princeton University.

UKPDS Group. UK Prospective Diabetes Study 33. Intensive blood-glucose control with sulphonylureas or insulin compared with conventional treatment and risk of complications in patients with type 2 diabetes. *Lancet* 1998;352: 837-853.

UKPDS Group. Effect of intensive blood-glucose control with metformin on complications in overweight patients with type 2 diabetes. *Lancet* 1998; 352:854-65.

UKPDS Group. UK Prospective Diabetes Study 16. Overview of 6 years' therapy of type II diabetes: a progressive disease. *Diabetes* 1995;44:1249-58 [Published erratum in *Diabetes* 1996;45:1249-58].

Wilcoxon, F. (1945). Individual comparisons by ranking methods. *Biometrics* 1, 80-3.

Yates, F. (1935). Complex experiments (with discussion). *Journal of the Royal Statistical Society, Series B* 2, 181-247.

We claim:

1. A method for titrating a multi-modality therapy regimen in an individual patient, comprising performing multiple times the steps of:

i) providing p modalities to said individual patient in a plurality of dose combinations;

ii) measuring one or more clinical endpoints in said individual patient;

iii) assigning, using a computer, measurements made in said measuring step for each of said one or more clinical endpoints to a desirability function;

iv) combining, using said computer, all desirability functions to obtain a composite desirability function for each of said plurality of dose combinations;

v) associating, using said computer, each composite desirability function with a vertex of a geometric figure, wherein said geometric figure has vertices, and wherein each of said vertices represents one of said plurality of dose combinations;

vi) outputting, using said computer, a next dose combination by applying an evolutionary operation direct search algorithm to said geometric figure; wherein performing steps i)-vi) multiple times constitutes titration of said multi-modality therapy regimen in said individual patient; and wherein results of said method are shown, displayed or represented as a plot, table or geometric representation, which enables a physician or researcher to evaluate and adjust said multi-modality therapy regimen for said individual patient.

2. The method of claim 1, wherein said next dose combination is generated, using said computer, by the evolutionary operation direct search algorithm moving away from a vertex which represents a least desirable dose combination through dose space to a new location, wherein said new location represents said next dose combination.

3. The method of claim 1 wherein said multi-modality therapy regimen is used to treat a combined modality therapy-requiring disease or condition selected from the group consisting of cancer, diabetes, asthma, AIDS, and hypertension.

4. The method of claim 1 wherein said dose combination comprises at least one exposure to radiation.

5. The method of claim 1 wherein said dose combination comprises at least one exercise regimen.

6. The method of claim 1 wherein said desirability function is generated from a logistic cumulative distribution function.

7. The method of claim 1 wherein said composite desirability function is unweighted.

8. The method of claim 1 wherein said composite desirability function is weighted.

9. The method of claim 1 wherein method is carried out in a plurality of individual patients.

10. A method for titrating a multi-modality therapy regimen in an individual patient, comprising performing multiple times the steps of:
   i) providing p modalities to said individual patient in a plurality of dose combinations;
   ii) measuring a clinical endpoint in said individual patient;
   iii) assigning, using said computer, said measurements obtained in said measuring step to a desirability function;
   iv) associating, using said computer, said measurements obtained in said measuring step for said clinical endpoint with a vertex of a geometric figure, wherein said geometric figure has vertices, and wherein each of said vertices represents one of said plurality of dose combinations; and
   v) outputting, using said computer, a next dose combination for said individual patient by applying an evolutionary operation direct search algorithm to said geometric figure, and
   vi) performing steps i)-v) multiple times, wherein performing steps i)-v) multiple times constitutes titration of said multi-modality therapy regimen in said individual patient; and wherein results of said method are shown, displayed or represented as a plot, table or geometric representation, which enables a physician or researcher to evaluate and adjust said multi-modality therapy regimen for said individual patient.

11. The method of claim 2 wherein said evolutionary operational direct search algorithm is the Nelder-Mead algorithm, said geometric figure is a simplex, and said number of said plurality of dose combinations is p +1.

12. The method of claim 10, wherein said next dose combination is generated, using said computer, by the evolutionary operation direct search algorithm moving away from a vertex which represents a least desirable dose combination through dose space to a new location, wherein said new location represents said next dose combination.

13. The method of claim 12, wherein said evolutionary operational direct search algorithm is the Nelder-Mead algorithm, said geometric figure is a simplex, and said number of said plurality of dose combinations is p +1.

14. The method of claim 1, further comprising the steps of performing steps i) through vii) in a plurality of patients;
constructing, using said computer, a confidence ellipsoid about a central location of final dose combinations in p-dimensional dose space; and
evaluating said confidence ellipsoid to determine
   whether a combination of p modalitites is better than no treatment at all; or
   whether a combination of p modalities is better than a combination of fewer than p modalities.

15. The method of claim 10, further comprising the steps of performing said steps of said method in a plurality of patients;
constructing, using said computer, a confidence ellipsoid about a central location of final dose combinations in p-dimensional dose space; and
evaluating said confidence ellipsoid to determine
   whether a combination of p modalitites is better than no treatment at all; or
   whether a combination of p modalities is better than a combination of fewer than p modalities.

16. The method of claim 1, further comprising the steps of performing steps i) through vi) in a plurality of patients; and statistically testing for an improvement in response.

17. The method of claim 10, further comprising the step of statistically testing for an improvement in response.

18. A method for titrating a multi-modality therapy regimen in a plurality of patients, comprising the steps of:
   i) providing p modalities to an individual patient in a plurality of dose combinations;
   ii) measuring a clinical endpoint in said individual patient;
   iii) assigning, using a computer, measurements obtained in said measuring step to a desirability function;
   iv) associating, using said computer, said measurements made obtained in said measuring step for said clinical endpoint with a vertex of a geometric figure, wherein said geometric figure has vertices, wherein each of said vertices represents one of said plurality of dose combinations; and
   v) determining, using said computer, a next dose combination for said individual patient by applying an evolutionary operation direct search algorithm to said geometric figure, and
   vi) performing steps i)-v) multiple times, wherein said step of performing each of said steps constitutes titration of said multi-modality therapy regimen in said individual patient; and wherein results of said method are shown, displayed or represented as a plot, table or geometric representation, which enables a physician or researcher to evaluate and adjust said multi-modality therapy regimen for said individual patient;
   vii) performing said steps i)-vi) of said method in each individual in said plurality of patients;
   viii) constructing, using said computer, a confidence ellipsoid about a central location of final dose combinations for said plurality of patients in p-dimensional dose space; and ix) evaluating said confidence ellipsoid to determine
      whether a combination of p modalitites is better than no treatment at all; or
      whether a combination of p modalities is better than a combination of fewer than p modalities.

19. The method of claim 18 further comprising the step of assigning, using said computer, said measurements obtained in said measuring step to a desirability function prior to associating, using said computer, said measurements with a vertex of said geometric figure.

20. The method of claim 18, wherein said next dose combination is generated, using said computer, by the evolutionary operation direct search algorithm moving away from a vertex which represents a least desirable dose combination through dose space to a new location, wherein said new location represents said next dose combination.

21. The method of claim 20, wherein said evolutionary operational direct search algorithm is the Nelder-Mead algorithm, said geometric figure is a simplex, and said number of said plurality of dose combinations is p +1.

22. The method of claim 18, further comprising the step of statistically testing for an improvement in response.

* * * * *